US012075989B2

(12) United States Patent
Whitmore et al.

(10) Patent No.: US 12,075,989 B2
(45) Date of Patent: Sep. 3, 2024

(54) ULTRASOUND TRANSPERINEAL PUNCTURE DEVICE GUIDE WITH A PIVOTABLE NEEDLE HOLDER

(71) Applicant: CIVCO Medical Instruments Co., Inc., Kalona, IA (US)

(72) Inventors: Willet Whitmore, Longboat Key, FL (US); Tim Meder, Riverside, IA (US); Paul Smith, North Liberty, IA (US); Sam Moody, Cedar Rapids, IA (US); Hannah Pankow, Iowa City, IA (US); Mackenzie Myhre, New York, NY (US); Caroline Myrand, St-Bruno-de-Montarville (CA)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 0 days.

(21) Appl. No.: 17/532,421

(22) Filed: Nov. 22, 2021

(65) Prior Publication Data
US 2022/0160339 A1 May 26, 2022

Related U.S. Application Data

(60) Provisional application No. 63/233,173, filed on Aug. 13, 2021, provisional application No. 63/116,980, filed on Nov. 23, 2020.

(51) Int. Cl.
*A61B 10/02* (2006.01)
*A61B 17/34* (2006.01)

(52) U.S. Cl.
CPC ...... *A61B 10/0233* (2013.01); *A61B 17/3403* (2013.01); *A61B 2017/3407* (2013.01); *A61B 2017/3413* (2013.01)

(58) Field of Classification Search
CPC .......... A61B 8/12; A61B 8/44; A61B 8/0841; A61B 10/0233; A61B 17/3403;
(Continued)

(56) References Cited

U.S. PATENT DOCUMENTS

| 4,911,173 A | 3/1990 | Terwilliger |
|---|---|---|
| 5,494,039 A | 2/1996 | Onik et al. |

(Continued)

FOREIGN PATENT DOCUMENTS

| AU | 2015240520 B2 | 2/2019 |
|---|---|---|
| AU | 2019203558 A1 | 7/2019 |

(Continued)

OTHER PUBLICATIONS

International Search Report and Written Opinion issued in corresponding International Application No. PCT/US2021/060324, mailed on Feb. 28, 2022, 12 pages.

(Continued)

*Primary Examiner* — Serkan Akar
*Assistant Examiner* — Neshat Baset
(74) *Attorney, Agent, or Firm* — BENESCH FRIEDLANDER, COPLAN & ARONOFF LLP

(57) ABSTRACT

A puncture device guide includes a guide platform configured to releasably attach to an ultrasound probe, a guide tower slidingly coupled to the guide platform, and a needle holder device for coupling to a puncture device. The guide tower projects upwardly from the guide platform and includes a vertical guidance slot and a plurality of attachment positions for engaging the needle holder device.

19 Claims, 15 Drawing Sheets

(58) Field of Classification Search
CPC . A61B 90/11; A61B 90/57; A61B 2017/3407; A61B 2017/3413; A61B 2017/3405; A61B 2017/3409; A61B 2090/378
See application file for complete search history.

(56) References Cited

U.S. PATENT DOCUMENTS

| | | | |
|---|---|---|---|
| 5,647,373 | A | 7/1997 | Paltieli |
| 5,800,389 | A | 9/1998 | Burney et al. |
| 6,398,711 | B1 | 6/2002 | Green et al. |
| 6,475,152 | B1 | 11/2002 | Kelly et al. |
| 6,702,749 | B2 | 3/2004 | Paladini et al. |
| 7,833,168 | B2 | 11/2010 | Taylor et al. |
| 7,981,041 | B2 | 7/2011 | McGahan |
| 9,198,688 | B2 | 12/2015 | Robinson |
| 9,655,595 | B2 | 5/2017 | Glossop et al. |
| 9,788,812 | B2 * | 10/2017 | Orome ............. A61B 5/150503 |
| 10,064,681 | B2 | 9/2018 | Allaway |
| 10,159,469 | B2 | 12/2018 | Stoianovici et al. |
| 10,743,909 | B2 | 8/2020 | Allaway |
| 10,743,910 | B2 | 8/2020 | Allaway |
| 10,743,911 | B2 | 8/2020 | Allaway |
| 2003/0139642 | A1 | 7/2003 | Hogendijk et al. |
| 2004/0143150 | A1 * | 7/2004 | Barzell ................ A61N 5/1027 600/7 |
| 2004/0167542 | A1 | 8/2004 | Solar et al. |
| 2004/0220444 | A1 | 11/2004 | Hogendijk et al. |
| 2006/0241477 | A1 * | 10/2006 | Sasady ................ A61B 17/3403 600/464 |
| 2007/0233157 | A1 | 10/2007 | Mark et al. |
| 2009/0093715 | A1 | 4/2009 | Downey et al. |
| 2010/0041990 | A1 * | 2/2010 | Schlitt ................ A61B 17/3403 600/461 |
| 2011/0319759 | A1 | 12/2011 | Liu et al. |
| 2012/0059260 | A1 | 3/2012 | Robinson |
| 2012/0253100 | A1 * | 10/2012 | Chisholm ............ A61N 5/1027 600/8 |
| 2013/0150714 | A1 * | 6/2013 | Howlett ............... A61B 8/4483 600/439 |
| 2014/0034800 | A1 * | 2/2014 | Strong ................. A61N 5/1027 248/299.1 |
| 2015/0282880 | A1 | 10/2015 | Allaway |
| 2015/0366544 | A1 | 12/2015 | Yap et al. |
| 2016/0022309 | A1 | 1/2016 | Allaway |
| 2017/0035385 | A1 | 2/2017 | Sasady et al. |
| 2017/0340308 | A1 * | 11/2017 | Cermak .................. A61B 8/12 |
| 2018/0116630 | A1 * | 5/2018 | Dykes ..................... A61B 8/12 |
| 2018/0360557 | A1 | 12/2018 | Allaway |
| 2019/0231386 | A1 | 8/2019 | Allaway |
| 2019/0231387 | A1 | 8/2019 | Allaway |

FOREIGN PATENT DOCUMENTS

| | | | |
|---|---|---|---|
| CA | 2940211 A1 | 10/2015 | |
| DE | 102010008491 B4 * | 1/2018 | ......... A61B 17/3403 |
| EP | 3125811 A1 | 2/2017 | |
| JP | 2006075386 A | 3/2006 | |
| JP | 2007282741 A | 11/2007 | |
| RU | 2676632 C1 | 1/2019 | |
| WO | 2020181388 A1 | 9/2020 | |

OTHER PUBLICATIONS

"Reinventing Prostate Biopsy," Precision Point, Perineologic, accessed Dec. 6, 2020, <https://perineologic.com/precisionpoint/>.

* cited by examiner

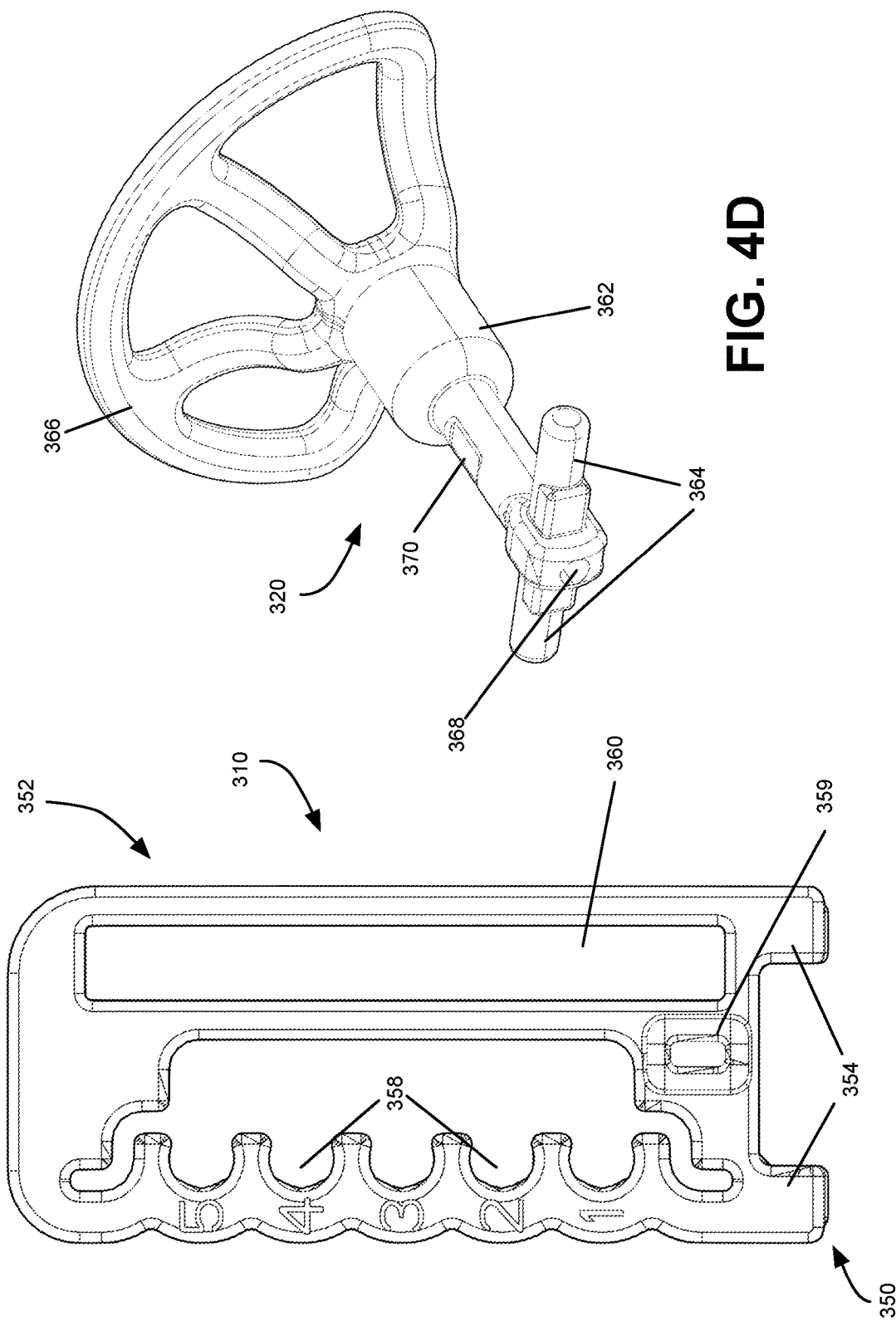

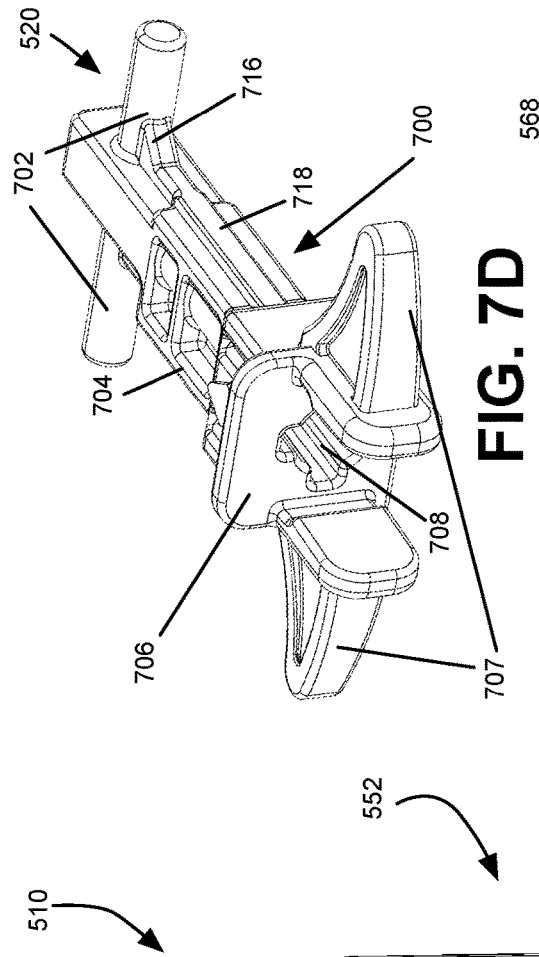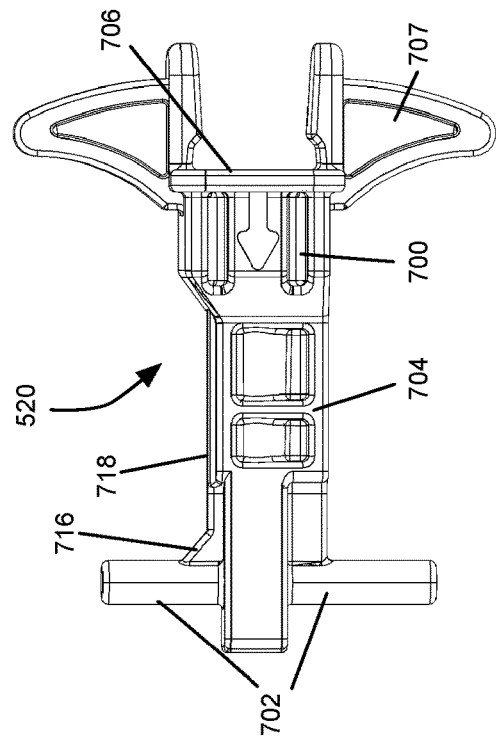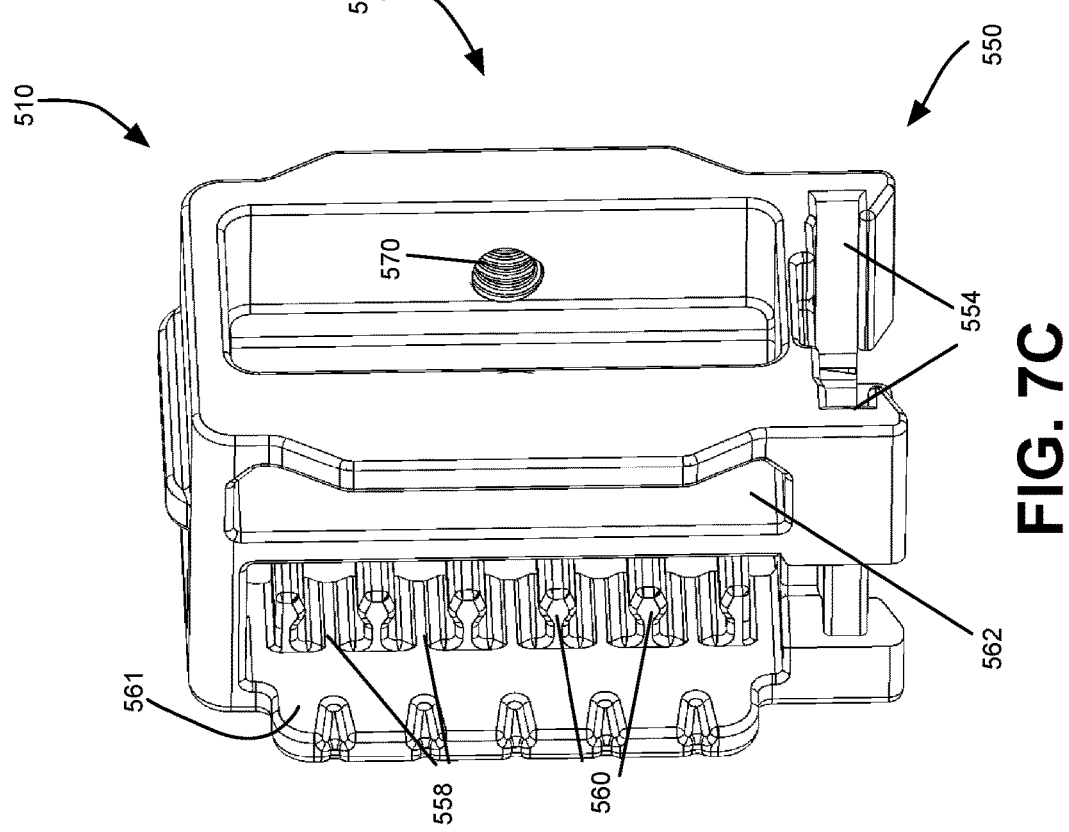

ULTRASOUND TRANSPERINEAL
PUNCTURE DEVICE GUIDE WITH A
PIVOTABLE NEEDLE HOLDER

CROSS-REFERENCE TO RELATED
APPLICATION

This application claims priority under 35 U.S.C. § 119, based on U.S. Provisional Patent Application No. 63/116,980 filed Nov. 23, 2020 and U.S. Provisional Patent Application No. 63/233,173 filed Aug. 13, 2021, both titled "TRANSPERINEAL PUNCTURE DEVICE GUIDE," the disclosures of which are hereby incorporated by reference.

BACKGROUND

This invention relates to puncture device guidance devices for use with medical imaging instruments and more particularly to devices for guiding puncture devices to repeatable locations on a patient relative to a medical imaging instrument probe.

Imaging instruments, such as ultrasound probes, have revolutionized the manner in which many important medical procedures are performed. These medical instruments utilize imaging techniques to explore and assess the condition of human tissue and/or organs. As a result, diagnostic and therapeutic protocols have been developed that allow many highly successful and safe procedures to be performed with minimal disturbance to patients. For example, ultrasound probes have become an accepted modality for exploring endocavities, e.g., the digestive and reproductive tracts, of humans and animals in order to conduct routine examinations, as well as to identify evidence of tumors or other tissue regions of interest.

The outpatient diagnostic procedure of transrectal (TR) ultrasound guided prostate biopsy, where the biopsy needle passes through the rectal wall, has become increasingly dangerous for the patient because, with the appearance of multi-drug resistant bacteria, the use of antibiotic prophylaxis has become less protective against post biopsy sepsis. As a direct consequence, the medical community has been developing a transperineal (TP) approach for biopsy. With this method, the biopsy needle passes through the perineal skin, that may be sterilized, avoiding the risk of infectious complication altogether. Meanwhile, the distinct advantages of transrectal ultrasound imaging for needle guidance are retained. Although a skilled operator may be able to perform a well targeted biopsy using a freehand technique for both the ultrasound imaging and the biopsy, it is quite difficult, often needing an extra set of hands. So, in the interests of patient safety, delivery of good anesthesia, standardization of technique for teaching purposes, consistent accuracy of the biopsies, and enabling the procedure being accomplished by a single operator, a mechanical guidance device that is connected to the ultrasound probe/transducer becomes essential, especially as this approach becomes widely relevant and adopted.

BRIEF DESCRIPTION OF THE DRAWINGS

FIGS. 4A, 4B, and 4C are first and second rear plan views and a right side plan view, respectively, of the guide tower of FIGS. 3A and 3B;

FIG. 4D is an isometric view of the needle holder device of FIGS. 3A and 3B

FIGS. 7A, 7B, and 7C are left and rear side plan and isometric views, respectively, of the guide tower of FIGS. 5A and 5B;

FIGS. 7D and 7E are isometric and top plan views, respectively, of the needle holder device of FIGS. 5A and 5B;

DETAILED DESCRIPTION OF THE
PREFERRED EMBODIMENTS

The following detailed description refers to the accompanying drawings. The same reference numbers in different drawings may identify the same or similar elements. Also, the following detailed description does not limit the invention.

Implementations described herein relate to guidance devices for facilitating the placement of a puncture device (e.g., a needle) at a defined position relative to an ultrasound probe. More specifically, the guidance devices described below include components that provide a number of paths relative to each other and at different defined distances from the ultrasound probe.

For example, in one implementation, the ultrasound probe may be a transrectal ultrasound probe and the guidance device may be configured to facilitate guidance of a biopsy needle at a location relative to the ultrasound probe. Consistent with embodiments described herein, the needle guidance device may include a plurality of selectable guidance paths while simultaneously enabling both fixed and parallel needle paths and angular adjustment of the needle while maintaining the angular orientation and axial relationship between the needle and the ultrasound probe. In addition, consistent with implementations described herein, the needle guidance device may be longitudinally advanceable at defined intervals.

Figure 1A:
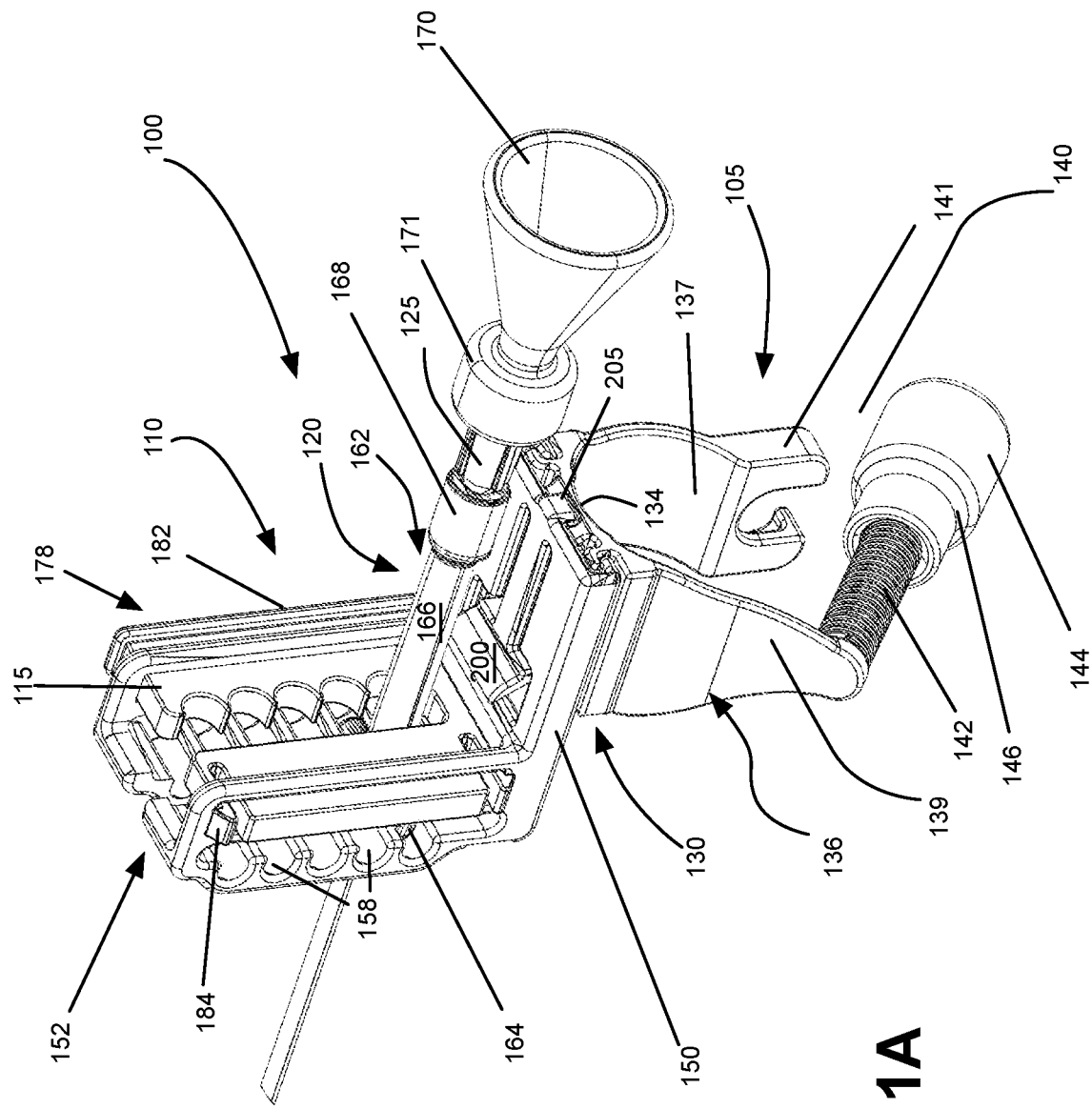
FIGS. 1A and 1B are isometric and exploded isometric views, respectively, illustrating a needle guidance device for use with an ultrasound probe, consistent with embodiments described herein.
Figure 1B:
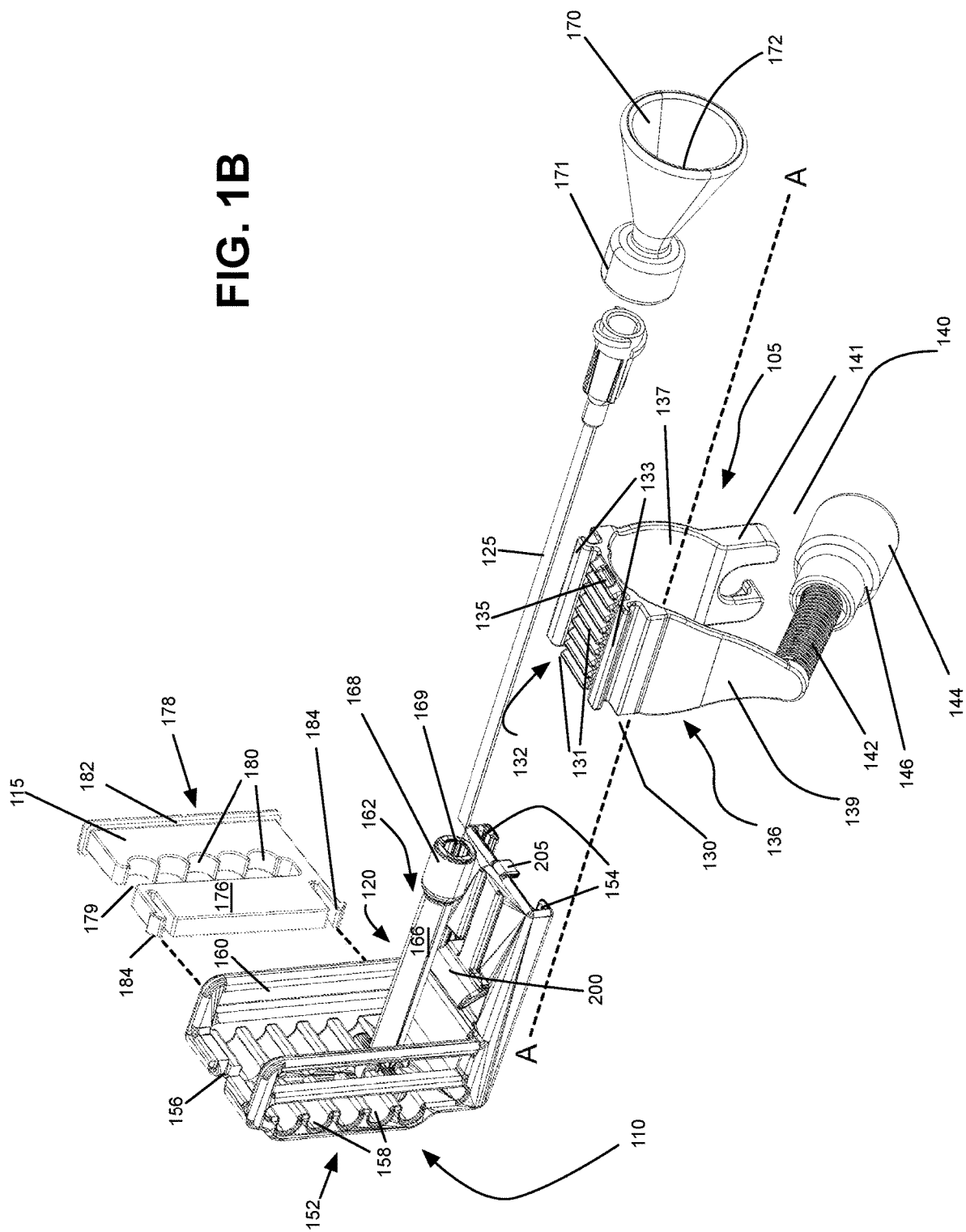

FIGS. 1A and 1B are isometric and exploded isometric views, respectively, illustrating a needle guidance device 100 for use with an ultrasound probe, consistent with embodiments described herein. As shown, needle guidance device 100 includes a clamping sleeve 105, a guide tower 110, an alignment plate 115, and a needle holder device 120. Prior to use, clamping sleeve 105 may be secured to an ultrasound probe (not shown) and guide tower 110 may be sliding coupled to clamping sleeve 105. As shown in FIGS.

1A and 1B, needle holder device 120 may be inserted into one of a plurality of path positions in guide tower 110. A trocar or other puncture device 125, such as a luer lock trocar needle may be received through needle holder device 120, as described below. Alignment plate 115 may be inserted into guide tower 110 to provide a guidance path that is parallel to the longitudinal axis of the ultrasound probe, as described below. During use, guide tower 110 may be slidingly advanced forward relative to clamping sleeve 105 and the ultrasound probe to engage the patient at a selected location. Upon completion of the procedure, the guide tower 110 may be retracted relative to clamping sleeve 105 and the ultrasound probe to disengage puncture device 125 from the patient.

Figure 2B:
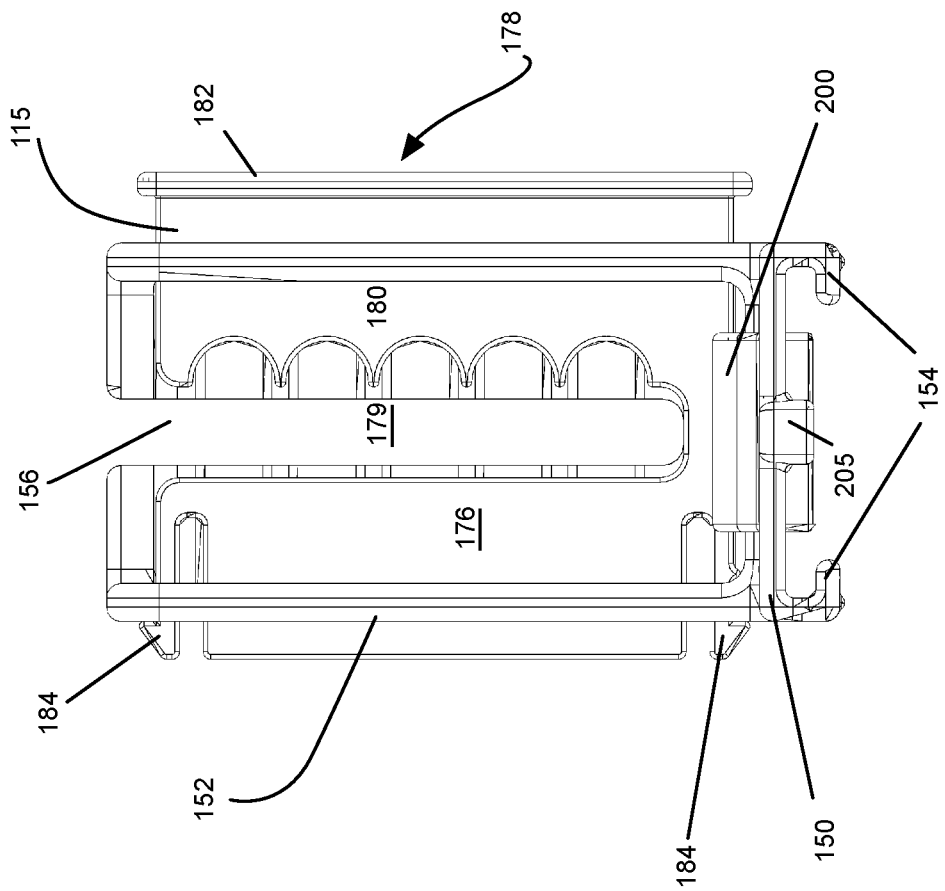
FIGS. 2A and 2B are bottom and rear views, respectively, of the guide tower of FIGS. 1A and 1B.
Figure 2A:
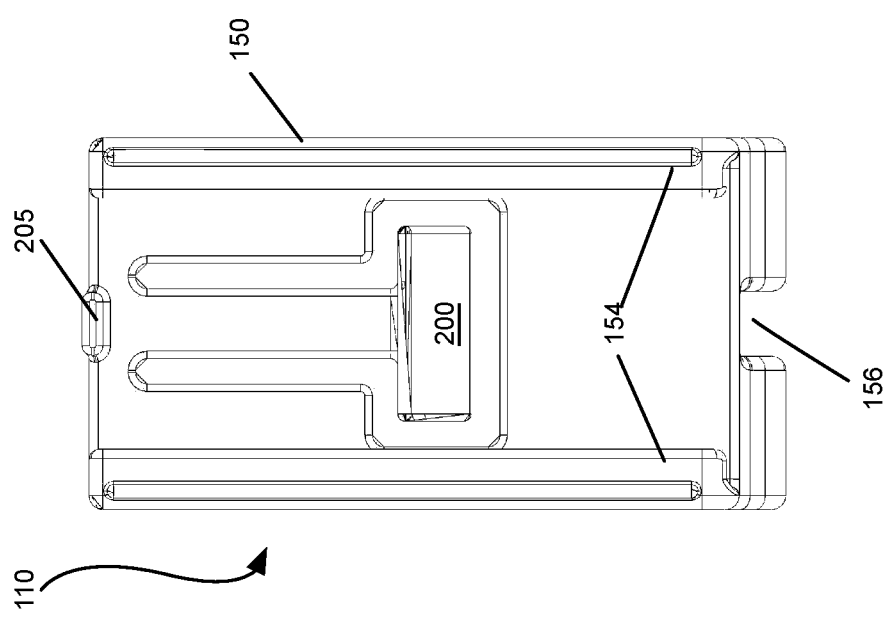

As shown in FIG. 1B, clamping sleeve 105 includes a mount portion 130, a strap portion 136, and a securement portion 140. As described herein, mount portion 130 may include an extruded configuration having an upper surface 132 and a lower surface 134. Upper surface 132 of mount portion 130 may be configured to support guide tower 110 in a longitudinally adjustable configuration. For example, as shown in FIG. 1B, upper surface 132 includes a pair of side rails 133 that project upwardly from upper surface 132. As described below, each of side rails 133 are configured for slidable receipt within corresponding side rails 154 in guide tower 110, as shown in FIG. 2A. To prevent guide tower 110 from moving too loosely relative to mount portion 130 during use, tolerances of respective side rails 133 may be such that a frictional relationship exists between mount portion 130 and guide tower 110 that resists undesirable movement.

In another implementation, as shown in FIG. 1B, upper surface 132 of mount portion 130 may include a plurality of longitudinally spaced barbed fixation elements 131 that project upwardly therefrom. Barbed fixation elements 131 are configured for engagement by a spring clip element 200 in guide tower 110, as shown in FIG. 2A. In some implementations, upper surface 132 of mount portion 130 may also include a stop engagement portion 135 for engaging a stop element 205 that projects downwardly from a lower surface of guide tower 110, as shown in FIG. 2A. When stop element 205 in guide tower 110 abuts stop engagement portion 135 in clamping sleeve 105, guide tower 110 is prevented from moving forward relative to clamping sleeve 105 and, thus, relative to the ultrasound probe to which the clamping sleeve is secured.

In other implementations, other mechanisms for securing guide tower 110 to clamping sleeve 105 may be used. For example, a combination of projections and detents or apertures may be used, such as that described above in relation to the embodiments of FIGS. 1B and 2A, to allow for releasable securement of guide tower 110 to mount portion 130.

Lower surface 134 of mount portion 130 includes a generally curved configuration that corresponds to a curved outer configuration of at least a portion of the transducer probe (not shown). Consistent with embodiments described herein, lower surface 134 may include a longitudinal channel or groove to create a defined space between the transducer probe and needle guidance device 100 sufficient to accommodate procedure accessory devices, such as a brachyballoon or the like.

Strap portion 136 of clamping sleeve 105 may include a generally resilient or flexible configuration that adaptively conforms to the outer surface of a portion of the transducer probe on which needle guidance device 100 is mounted. In particular, strap portion 136 may include a first lateral portion 137 extending from a first side of mount portion 130 and a second lateral portion 139 extending from a second side of mount portion 130 opposite to first lateral portion 137. First and second lateral portions 137/139 may collectively terminate in securement portion 140. As shown in FIGS. 1A and 1B, in one implementation, securement portion 140 may include a collar portion 140 formed at the terminus of first lateral portion 137 and a threaded portion 142 formed at the terminus of second lateral portion 139. Collar portion 140 may include an opening adapted to receive an end of threaded portion 142 during mounting of clamping sleeve 105 onto the ultrasound probe.

To secure clamping sleeve 105 to an ultrasound probe, lower surface 134 of the mount portion 130 and the inside surface of first lateral portion 137 are initially brought into contact with an outside surface of the ultrasound probe. The second lateral portion 139 is then flexed such that its inside surface also contacts the outer surface of the ultrasound probe, thereby causing threaded portion 142 to enter collar portion 140. A clamping nut 144 having a mating collar portion 146 is threadedly advanced on threaded portion 142, to cause the collar portion 146 on clamping nut 144 to clampingly engage collar portion 140 in first lateral portion 137, thus securing clamping sleeve 105 to the ultrasound probe. When it is desired to remove clamping sleeve 105, clamping nut 144 may be reversed, thereby releasing collar portion 140.

Consistent with implementations described herein, one or more of lateral portions 137/139 may be formed in a thickness sufficient to allow flexure. In some implementations, only second lateral portion 139 is formed to enable flexure, with first lateral portion 137 having a substantially rigid configuration. In some embodiments, an entirety of clamping sleeve 105, with the exception of clamping nut 144, may be integrally formed, such as via injection molding, 3D printing, etc.

As shown in FIGS. 1A and 1B, guide tower 110 includes a substantially L-shaped configuration for providing a secure interface to clamping sleeve 105 and a plurality of radially spaced (relative to a longitudinal orientation of the ultrasound probe, as depicted by line A-A in FIG. 1B) needle guide paths for engaging needle holder device 120, as described herein. In particular, guide tower 110 includes a sleeve interface portion 150 having a generally planar configuration and a guide path portion 152 that projects upwardly from the sleeve interface portion 200. A lower surface of sleeve interface portion 150 includes opposing side rails 154 that project downwardly therefrom and are configured to interface with side rails 133 in clamping sleeve 105, as described above. In some implementations, side rails 154 have opposing c-shaped configurations that capture side rails 133 and prevent relative radial movement between clamping sleeve 105 and guide tower 110 when side rails 133 in mount portion 130 are positioned within side rails 154 in guide tower 110, while allowing sliding longitudinal movement therebetween.

As described above, and as shown in FIG. 2A, which depicts a bottom view of guide tower 110, sleeve interface portion 150 includes a resilient spring clip element 600 configured to engage barbed fixation elements 131 that project upwardly from clamping sleeve 105.

In one implementation consistent with embodiments described herein, guide path portion 152 projects upwardly substantially perpendicularly from sleeve interface portion 150. As shown, in FIGS. 1A, 1B, and 2B (which depicts a rear view of guide tower 110 with alignment plate 115 position therein), guide path portion 152 includes a vertical guidance slot 156, a plurality of needle holder device receiving cups 158, and an alignment plate receiving slot 160.

Vertical guidance slot 156 is centrally aligned within guide tower 110 so as to be aligned with longitudinal ultrasound imaging crystals within a transducer to which the needle guide device 100 is affixed such that puncture device 125 (e.g., a trocar needle) designed to pass therethrough is consistently visualized in the imaging plane under typical imaging conditions. As shown in FIG. 2B, vertical guidance slot 156 extends substantially the entire height of guide tower 110 to allow an inserted puncture device to be freely moved between needle holder device guide device receiving cup positions.

As shown in FIG. 1B, needle holder device receiving cups 158 comprise pairs of aligned recesses or openings in guide path portion 152 and positioned on opposite sides of vertical guidance slot 156. Each pair of needle holder device receiving cups 158 is vertically spaced relative to the adjacent pair of needle holder device receiving cups 158 to provide a plurality of attachment positions for needle holder device 120, as described in additional detail below. In the present embodiment, five pairs of needle holder device receiving cups 158 are provided, although other implementations may include fewer or additional needle holder device receiving cups 158 may be provided. Consistent with implementations described herein, each needle holder device receiving cup 158 comprises a generally arced opening configured to receive respective portions of needle holder device 120, as described below. In some implementations, the dimensions of each needle holder device receiving cup 158 is such that needle holder device 120 is removable captured therein. For example, each needle holder device receiving cup 158 may be sized to provide a tight frictional fit to needle holder device 120. In other implementations, each needle holder device receiving cup 158 may have an opening whose arc is slightly more than 180°, such that the needle holder device 120 snaps into a respective pair of needle holder device receiving cups 158. In contrast to the needle guidance device 100 of FIGS. 1A-2B, needle holder device receiving cups 158 are positioned forwardly of alignment plate receiving slot 160.

As shown in FIG. 1B, alignment plate receiving slot 160 is configured to extend transversely within guide tower 110 in a position rearward of needle holder device receiving cups 158. Alignment plate receiving slot 160 is sized to receive alignment plate 115 therein. As described in additional detail below, upon receipt of a needle holder device 120 and corresponding puncture device 125 within a particular pair of needle holder device receiving cups 158, alignment plate 115 may be advanced within alignment plate receiving slot 160 to positively support puncture device 125 in a defined path relative to ultrasound probe. For example, in some implementations, the configuration of alignment plate 115 forces puncture device 125 into a parallel path, although different configurations of may be used to accommodate different path angles. As shown in FIG. 1B, in one implementation, alignment plate receiving slot 160 includes an outer rim portion 161 configured to receive a portion of alignment plate 115 at a defined depth within alignment plate receiving slot 160.

Figure 2C:
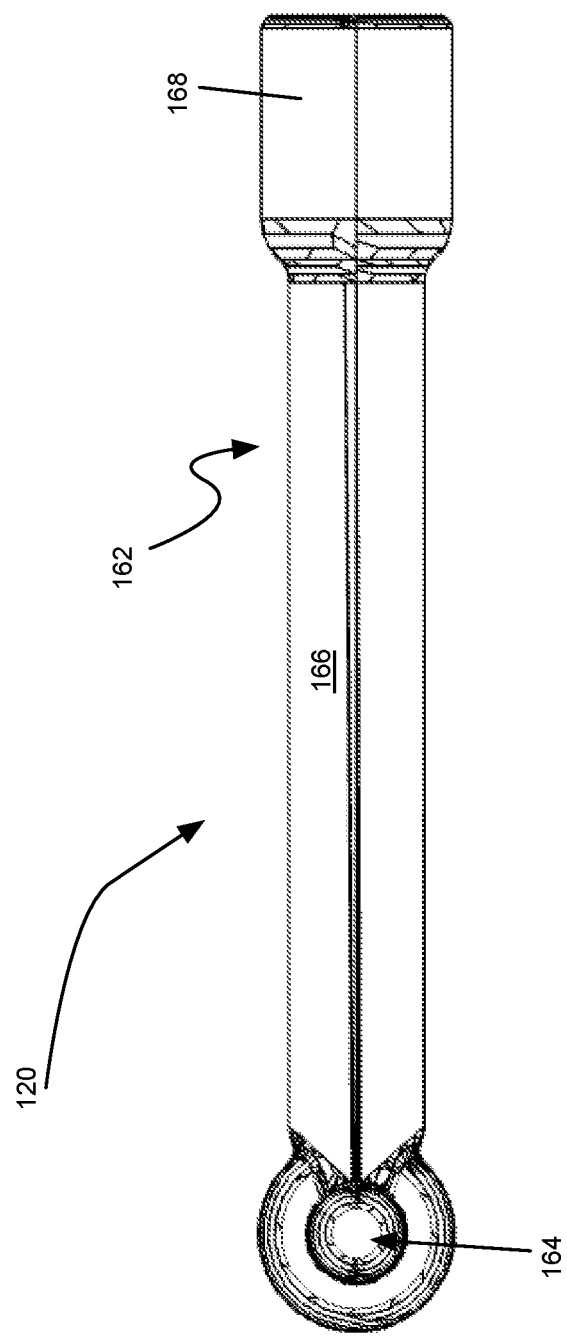
FIG. 2C is a side view of the trocar guide device of FIGS. 1A and 1B.

FIG. 2C is a side view of needle holder device 120 consistent with embodiments described herein. As shown in FIGS. 1A, 1B, and 2C needle holder device 120 comprises an adapter for coupling to guide tower 110 and for receiving puncture device 125. In some implementations, needle holder device 120 may be configured to receive a trocar puncture device therethrough.

In one implementation, needle holder device 120 includes a body portion 162, engagement shoulders 164, handle portion 166, and flanged portion 168. As shown, body portion 162 includes a generally tubular element having a central aperture 169 therethrough. Body portion 162 is configured receive puncture device 125 within central aperture 169. A forward end of body portion 162 terminates in engagement shoulders 164 and a rearward end of body portion terminates in flange portion 162. An outer surface of an intermediate portion of body portion 162 forms handle portion 166, which may be manipulated to effect proper placement of needle holder device 120 during use.

Engagement shoulders 164 include a pair of substantially cylindrical elements that project perpendicularly outwardly from opposing sides of the forward end of body portion 162. As shown in FIG. 1A and described generally above, engagement shoulders 164 are configured to be received within a selected pair of needle holder device receiving cups 158 during use. The cylindrical configuration of engagement shoulders 164 allows for upward and downward rotation of needle holder device 120 within receiving cups 158 via handle portion 166 if desired, and prior to advancement of alignment plate 115 within alignment plate receiving slot 160, which fixes the angular orientation of needle holder device 120.

As shown in FIGS. 1A, 1B, and 2C, consistent with implementations described herein, a funnel member 170 may be affixed to luer lock puncture device 125 prior to inserting within needle holder device 120. Consistent with embodiments described herein, funnel member 170 includes a puncture device interface portion 171 and a funnel aperture 172. Puncture device interface portion 171 includes a concentrically tubular structure for receiving an interface element of a puncture device 125, such as a luer lock. In this configuration, puncture device interface portion 171 includes internal threads (not shown) configured to engage and retain external threads on luer lock puncture device 125. Funnel aperture 172 includes a wide mouth aperture at the rearward end funnel member 170 having a larger inside diameter or circumference than central aperture (not shown) in body portion 162 for enabling easy entrance of a puncture device, such as biopsy needle or the like.

As shown in FIG. 1B, alignment plate 115 includes a body portion 176, an abutment portion 178, a free movement portion 179, and a plurality of path retaining channels 180. In general, body portion 176 includes a substantially planar element sized for receipt within alignment plate receiving slot 160. Abutment portion 178 includes a flange portion 182 that provides a surface for abutting an outer rim portion 161 of alignment plate receiving slot 160 when alignment plate 115 is fully inserted into alignment plate receiving slot 160.

Consistent with implementations described herein, free movement portion 179 includes a slotted opening that communicates with path retaining channels 180. Path retaining channels 180 include a plurality of arcuate recesses spaced to correspond to needle holder device receiving cups 158. The combination of free movement portion 179 and path retaining channels 180 provides two operational positions for alignment plate 115.

In a first position, alignment plate 115 is partially inserted into alignment plate receiving slot 160 such that free movement portion 179 is aligned with vertical guidance slot 160. This allows needle holder device 120 to be inserted into guide tower 110. Once needle holder device 120 has been inserted into guide tower 110 and into a selected pair of needle holder device receiving cups 158, alignment plate 115 is advanced within alignment plate receiving slot 160 (until flange portion 182 abuts outer rim portion 161). In this second position, needle holder device 120 is retained in a parallel path relative to the ultrasound probe. Although the position of the path retaining channels 180 in alignment plate 115 of the embodiment of FIGS. 1A and 1B provides for a parallel path for needle holder device 120, in other implementations, the positions of path retaining channels 180 may be offset with respect to needle holder device receiving cups 158 to provide other angular orientations.

Alignment plate 115 is configured to be persistently retained within alignment plate receiving slot 160. As shown in FIG. 1B, alignment plate 115 may include one or more spring clip portions 184 configured to engage a corresponding rim portion of slot 160 when alignment plate 115 is in the first position to prevent unintended removal of alignment plate 115 from alignment plate receiving slot 160.

During assembly and use, engagement shoulders 164 of needle holder device 120 are initially oriented vertically and needle holder device 120 is inserted into vertical guidance slot 156 and forwardly through alignment plate 115 when the alignment plate is in the first position. Needle holder device 120 is then rotated 90° and inserted into a selected pair of needle holder device receiving cups 158. Alignment plate 115 is then advanced into the second position, thus capturing the needle holder device 120 into a selected parallel path.

After puncture device 125 is seated within a selected parallel path within guide tower 110 (e.g., within a selected pair of needle holder device receiving cups 158 and locked by alignment plate 115), guide tower 110 is slidingly advanced forward relative to clamping sleeve 105 and the ultrasound probe to engage (e.g., puncture) the patient at a selected location. The guide tower is further advanced until a tip of puncture device 125 reaches a desired depth within patient or until stop 205 in guide tower 110 abuts stop engagement portion 135 in clamping sleeve 105.

Consistent with embodiments described herein, following patient puncture, alignment plate 115 may be returned to its first, non-locking position. Needle holder device 120 may then be pivoted about needle holder device receiving cups 158 or removed from needle holder device receiving cups 158 and moved to a new vertical position without requiring a second puncture.

Figure 3A:
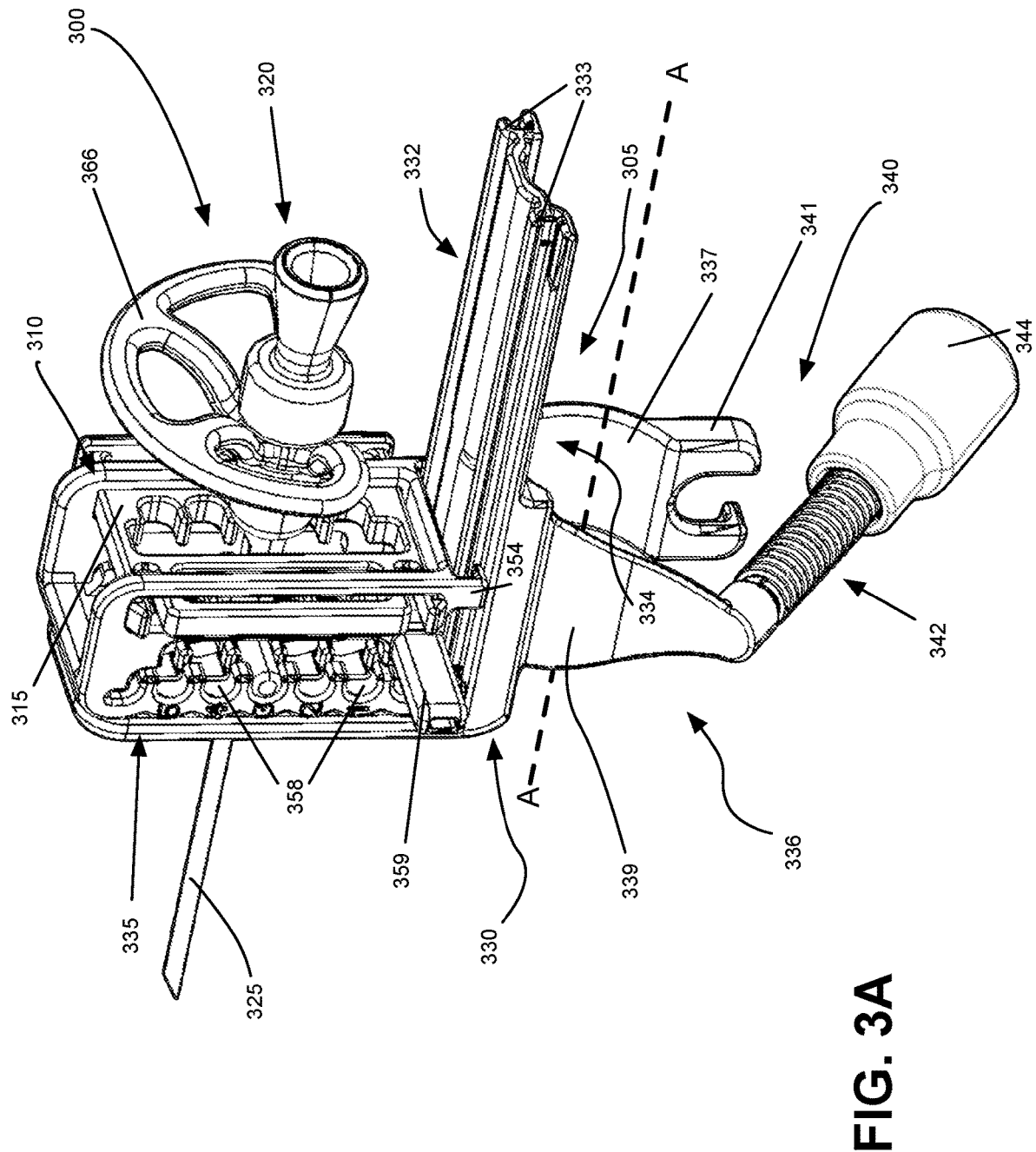
FIGS. 3A and 3B are isometric and exploded isometric views, respectively, illustrating another embodiment of a needle guidance device for use with an ultrasound probe, consistent with embodiments described.
Figure 3B:
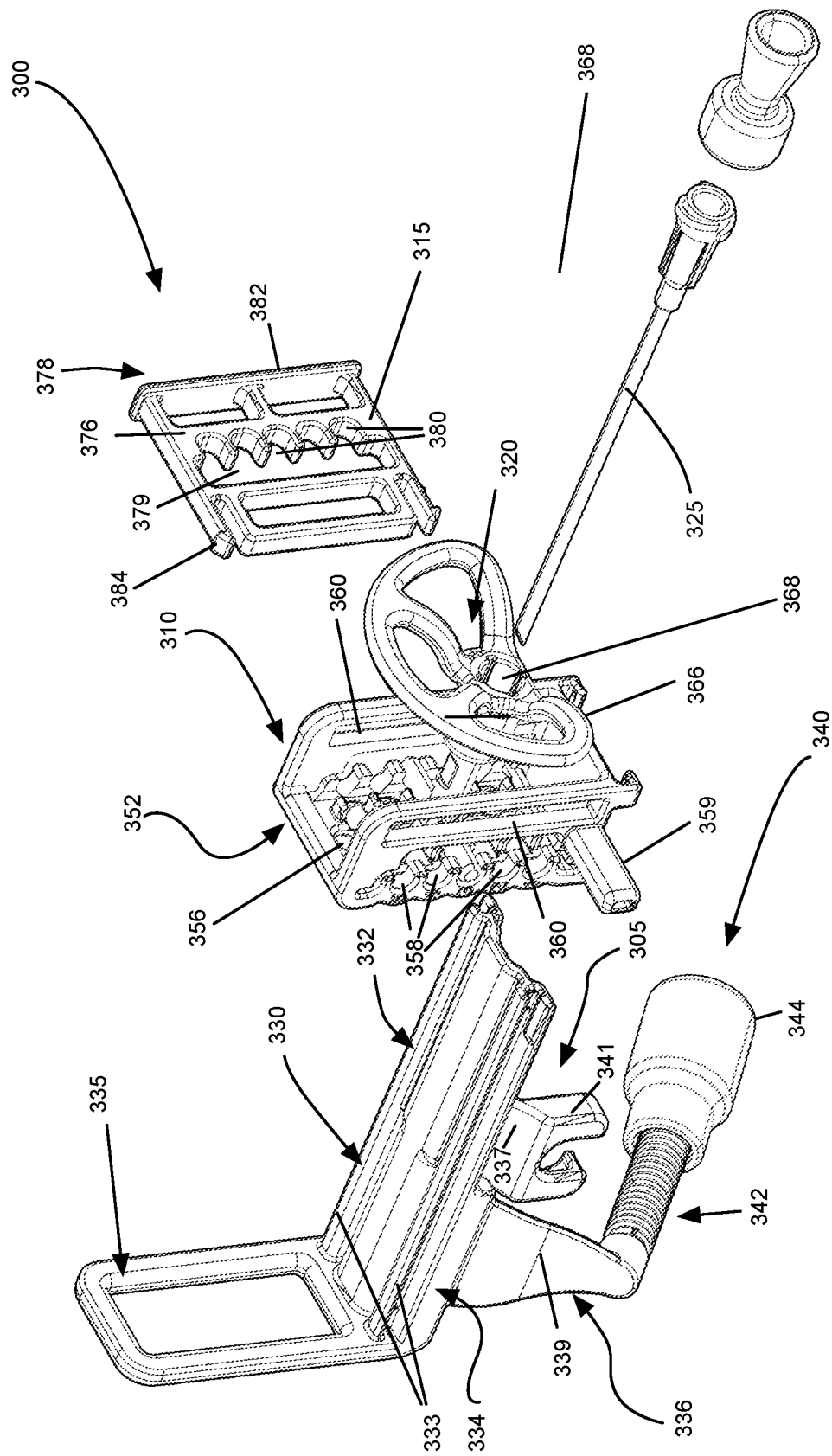

FIGS. 3A and 3B are isometric and exploded isometric views, respectively, illustrating another embodiment of a needle guidance device 300 for use with an ultrasound probe, consistent with embodiments described herein. As shown, needle guidance device 300 includes a guide platform 305, a guide tower 310, an alignment plate 315, and a needle holder device 320. Prior to use, guide platform 305 may be secured to an ultrasound probe (not shown) and guide tower 310 may be sliding coupled to guide platform 305. As shown in FIGS. 3A and 3B, needle holder device 320 may be inserted into one of a plurality of path positions in guide tower 310. A trocar or other puncture device 325, such as a luer lock trocar needle may be received through needle holder device 320, as described below. In other implementations, puncture device 325 may be formed together with needle holder device 320, as an integral unit, such that the puncture device 325 is not independently removable from needle holder device 320. Alignment plate 315 may be inserted into guide tower 310 to provide a guidance path that is parallel to the longitudinal axis of the ultrasound probe, as described below. During use, guide tower 310 may be slidingly advanced forward relative to guide platform 305 and the ultrasound probe to engage the patient at a selected location. Upon completion of the procedure, the guide tower 310 may be retracted relative to guide platform 305 and the ultrasound probe to disengage puncture device 325 from the patient.

As shown in FIG. 3B, guide platform 305 includes a mount portion 330, a strap portion 336, and a securement portion 340. As described herein, mount portion 330 may include a longitudinally extruded configuration having an upper surface 332 and a lower surface 334. Upper surface 332 of mount portion 330 may be configured to support guide tower 310 in a longitudinally adjustable configuration. For example, as shown in FIG. 3B, upper surface 332 includes a pair of side rails 333 that project upwardly from upper surface 332. As described below, each of side rails 333 are configured for slidable receipt within corresponding side rails 354 in guide tower 310, as shown in FIG. 4A. To prevent guide tower 310 from moving too loosely relative to mount portion 330 during use, tolerances of respective side rails 333 may be such that a frictional relationship exists between mount portion 330 and guide tower 310 that resists undesirable movement. In other implementations, other mechanisms for securing guide tower 310 to guide platform 305 may be used. For example, a combination of projections and detents or apertures may be used to allow for releasable securement of guide tower 310 to mount portion 330.

As shown in FIGS. 3A and 3B, the forward end of mount surface 330 may include a stabilization feature 335 that projects perpendicularly upwardly from upper surface 332. Stabilization feature 335 may have a large central aperture therein for allowing puncture device 325 to move freely therethrough. During use, a forward end of stabilization feature 335 is configured to engage a patient (e.g., a patient's perineum) to stabilize the relationship between needle guidance device 300 and the patient. In addition, a rearward end of stabilization feature 335 further provides a positive stop to longitudinal movement of guide tower 310 relative to guide platform 305.

Lower surface 334 of mount portion 330 includes a generally curved configuration that corresponds to a curved outer configuration of at least a portion of the transducer probe (not shown). Strap portion 336 of guide platform 305 may include a generally resilient or flexible configuration that adaptively conforms to the outer surface of a portion of the transducer probe on which needle guidance device 300 is mounted. In particular, strap portion 336 may include a first lateral portion 337 extending from a first side of mount portion 330 and a second lateral portion 339 extending from a second side of mount portion 330 opposite to first lateral portion 337. First and second lateral portions 337/339 may collectively terminate in securement portion 340. As shown in FIGS. 3A and 3B, in one implementation, securement portion 340 may include a collar portion 341 formed at the terminus of first lateral portion 337 and a threaded portion 342 formed at the terminus of second lateral portion 339. Collar portion 341 may include an opening adapted to receive an end of threaded portion 342 during mounting of guide platform 305 onto the ultrasound probe.

To secure guide platform 305 to an ultrasound probe, lower surface 334 of the mount portion 330 and the inside surface of first lateral portion 337 are initially brought into contact with an outside surface of the ultrasound probe. The second lateral portion 339 is then flexed such that its inside surface also contacts the outer surface of the ultrasound probe, thereby causing threaded portion 342 to enter collar portion 341. A clamping nut 344 having a mating collar portion 346 is threadedly advanced on threaded portion 342, to cause the collar portion 346 on clamping nut 344 to clampingly engage collar portion 341 in first lateral portion 337, thus securing guide platform 305 to the ultrasound probe. When it is desired to remove guide platform 305, clamping nut 344 may be reversed, thereby releasing collar portion 341.

Consistent with implementations described herein, one or more of lateral portions 337/339 may be formed in a thickness sufficient to allow flexure. In some implementations, only second lateral portion 339 is formed to enable flexure, with first lateral portion 337 having a substantially rigid configuration. In some embodiments, an entirety of guide platform 305, with the exception of clamping nut 344, may be integrally formed, such as via injection molding, 3D printing, etc.

Figure 4B:
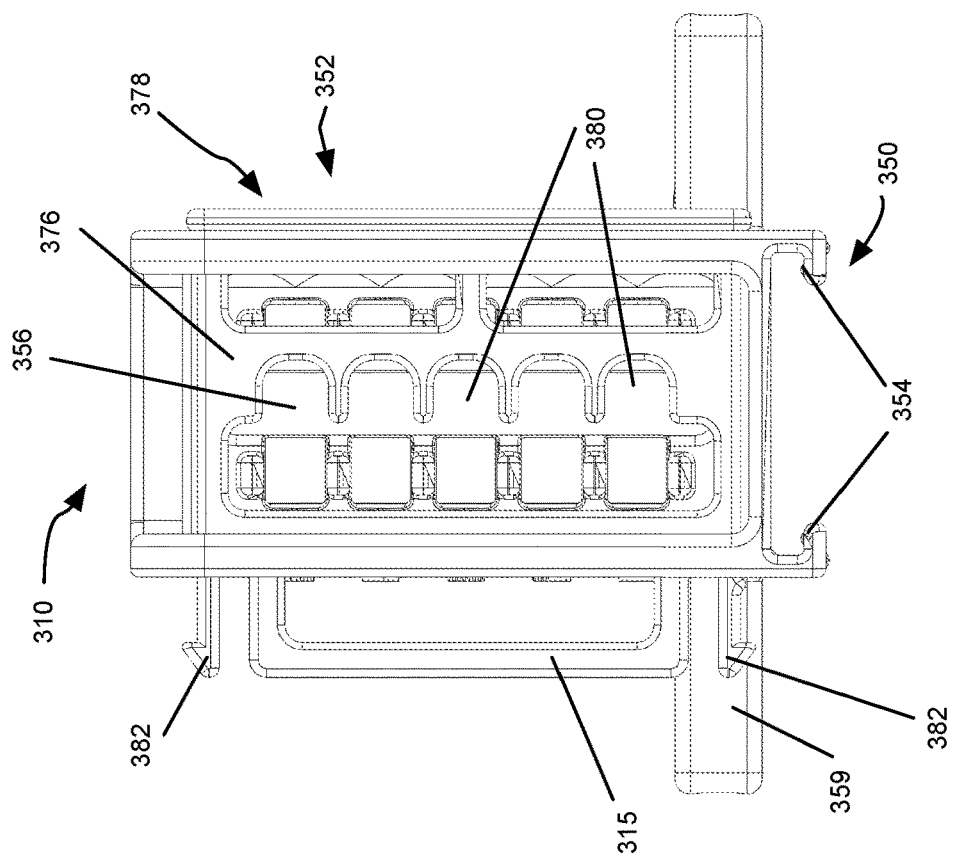
Figure 4A:
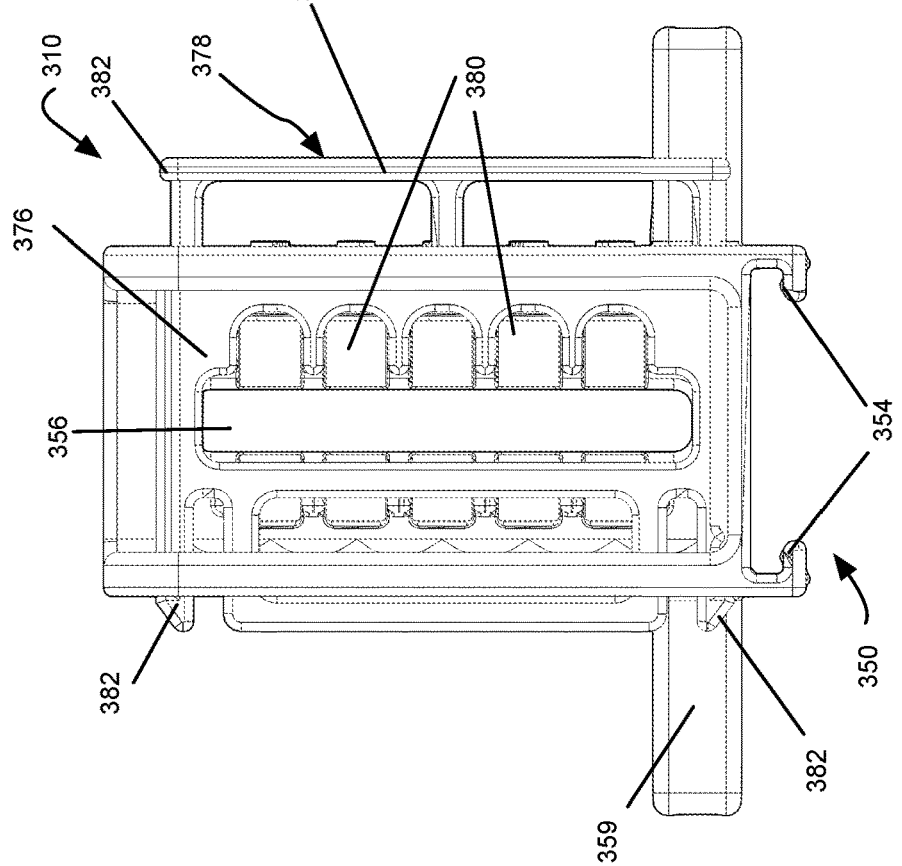

FIGS. 4A and 4B are rear plan views of guide tower 310 with alignment plate in unlocked and locked positions, respectively. FIG. 4C is a side view of guide tower 310. As shown in FIGS. 3A, 3B, and 4A-4C, guide tower 310 includes a substantially frame-like configuration for providing a secure interface to guide platform 305 and a plurality of spaced (relative to a longitudinal orientation of the ultrasound probe, as depicted by line A-A in FIG. 3A) needle guide paths for engaging needle holder device 320, as described herein. In particular, guide tower 310 includes a platform interface portion 350 and a guide path portion 352 that projects upwardly from the platform interface portion 350. A lower surface of platform interface portion 350 includes opposing side rails 354 that project downwardly therefrom and are configured to interface with side rails 333 in guide platform 305, as described above. In some implementations, side rails 354 have opposing c-shaped configurations that capture side rails 333 and prevent relative radial movement between guide platform 305 and guide tower 310 when side rails 333 in mount portion 330 are positioned within side rails 354 in guide tower 310, while allowing sliding longitudinal movement therebetween.

In one implementation consistent with embodiments described herein, guide path portion 352 projects upwardly substantially perpendicularly from platform interface portion 350. As shown in FIGS. 3B and 4B, guide path portion 352 includes a vertical guidance slot 356, a plurality of needle holder device receiving cups 358, tower advancement handles 359, and an alignment plate receiving slot 360.

Vertical guidance slot 356 is centrally aligned within guide tower 310 so as to be aligned with longitudinal ultrasound imaging crystals within a transducer to which the needle guide device 300 is affixed such that puncture device 325 (e.g., a trocar needle) designed to pass therethrough is consistently visualized in the imaging plane under typical imaging conditions. As shown in FIG. 4B, vertical guidance slot 356 extends substantially the entire height of guide tower 310 to allow an inserted puncture device to be freely moved between needle guide device receiving cup positions.

As shown in FIG. 3B, needle holder device receiving cups 358 comprise pairs of aligned recesses or openings in guide path portion 352 and positioned on opposite sides of vertical guidance slot 356. Each pair of needle holder device receiving cups 358 is vertically spaced relative to the adjacent pair of needle holder device receiving cups 358 to provide a plurality of attachment positions for needle holder device 320, as described in additional detail below. In the present embodiment, five pairs of needle holder device receiving cups 358 are provided, although other implementations may include fewer or additional needle holder device receiving cups 358 may be provided. Consistent with implementations described herein, each needle guide device receiving cup 358 comprises a generally arced opening configured to receive respective portions of needle holder device 320, as described below. In some implementations, the dimensions of each needle guide device receiving cup 358 is such that needle holder device 320 is removable captured therein. For example, each needle guide device receiving cup 358 may be sized to provide a tight frictional fit to needle holder device 320. In other implementations, each needle guide device receiving cup 358 may have an opening whose arc is slightly more than 180°, such that the needle holder device 320 snaps into a respective pair of needle holder device receiving cups 358.

As shown in FIGS. 3A, 3B, and 4B, tower advancement handles 359 project laterally outwardly from guide tower 310 proximate to platform interface portion 350. During use, an operator may advance or retract guide tower 310 longitudinally along guide platform 305 manually by pushing or pulling on tower advancement handles 359, respectively.

As shown in FIG. 3B, alignment plate receiving slot 360 is configured to extend transversely within guide tower 310 in a position rearward of needle holder device receiving cups 358. Alignment plate receiving slot 360 is sized to receive alignment plate 315 therein. As described in additional detail below, upon receipt of a needle holder device 320 and corresponding puncture device 325 within a particular pair of needle holder device receiving cups 358, alignment plate 315 may be advanced within alignment plate receiving slot 360 to positively support puncture device 325 in a defined path relative to ultrasound probe. For example, in some implementations, the configuration of alignment plate 315 forces puncture device 325 into a parallel path, although different configurations of may be used to accommodate different path angles. In one implementation, alignment plate receiving slot 360 includes an outer rim portion configured to receive a portion of alignment plate 315 at a defined depth within alignment plate receiving slot 360. FIG. 4D is an isometric view of needle holder device 320 consistent with embodiments described herein. As shown in FIGS. 3A, 3B, and 4D needle holder device 320 comprises an adapter for coupling to guide tower 310 and for receiving puncture device 325. In some implementations, needle holder device 320 may be configured to receive a puncture device therethrough.

In one implementation, needle holder device 320 includes a body portion 362, engagement shoulders 364, and handle portion 366. As shown, body portion 362 includes a generally tubular element having a central aperture 368 therethrough. Body portion 362 is configured to receive puncture device 325 within central aperture 368. A forward end of body portion 362 terminates in engagement shoulders 364 and a rearward end of body portion terminates in handle portion 366, which may be manipulated to effect proper placement of needle holder device 320 during use. As shown in FIG. 4D, intermediate portion of body portion 362 may include an alignment plate engaging surface 370 for engaging path retaining channels 380 in alignment plate 315, as described below.

For example, handle portion 366 may be used to insert and remove engagement shoulders 364 from needle holder device receiving cups 358, to rotate needle guide device to allow removal from guide tower 310, to raise and lower needle holder device 320 between needle holder device receiving cups 358 and to affect manual angular deflection of needle holder device 320.

Engagement shoulders 364 include a pair of substantially cylindrical elements that project perpendicularly outwardly from opposing sides of the forward end of body portion 362.

As shown in FIG. 3A and described generally above, engagement shoulders 364 are configured to be received within a selected pair of needle holder device receiving cups 358 during use. The cylindrical configuration of engagement shoulders 364 allows for upward and downward rotation of needle holder device 320 within receiving cups 358 via handle portion 366 if desired, and prior to advancement of alignment plate 315 within alignment plate receiving slot 360, which fixes the angular orientation of needle holder device 320.

As shown in FIGS. 3B, 4A, and 4B, alignment plate 315 includes a body portion 376, an abutment portion 378, a free movement portion 379, and a plurality of path retaining channels 380. In general, body portion 376 includes a substantially planar element sized for receipt within alignment plate receiving slot 360. Abutment portion 378 includes a flange portion 382 that provides a surface for abutting an outer rim portion of alignment plate receiving slot 360 when alignment plate 315 is fully inserted into alignment plate receiving slot 360.

Consistent with implementations described herein, free movement portion 379 includes a slotted opening that communicates with path retaining channels 380. Path retaining channels 380 include a plurality of arcuate recesses spaced to correspond to needle holder device receiving cups 358. The combination of free movement portion 379 and path retaining channels 380 provides two operational positions for alignment plate 315.

In a first position, alignment plate 315 is partially inserted into alignment plate receiving slot 360 such that free movement portion 379 is aligned with vertical guidance slot 356. This allows needle holder device 320 to be inserted into guide tower 310 via handle portion 366. Once needle holder device 320 has been inserted into guide tower 310 and into a selected pair of needle holder device receiving cups 358, alignment plate 315 is advanced within alignment plate receiving slot 360 (until flange portion 382 abuts the outer rim portion of alignment plate receiving slot 360). In this second position, a path retaining channel 380 corresponding to the particular pair of needle holder device receiving cups 358 engages alignment plate engaging surface 370 of needle holder device 320 to retained needle holder device 320 in a parallel path relative to the ultrasound probe.

Although the position of the path retaining channels 380 in alignment plate 315 of the embodiment of FIGS. 3A and 3B provides for a parallel path for needle holder device 320, in other implementations, the positions of path retaining channels 380 may be offset with respect to needle holder device receiving cups 358 to provide other angular orientations.

As shown in FIGS. 3B, 4A, and 4B, alignment plate 315 may include one or more spring clip portions 384 configured to engage a corresponding rim portion of slot 360 when alignment plate 315 is in the first position to prevent unintended removal of alignment plate 315 from alignment plate receiving slot 360.

During assembly and use, engagement shoulders 364 of needle holder device 320 are initially oriented vertically and needle holder device 320 is inserted into vertical guidance slot 356 and forwardly through alignment plate 315 when the alignment plate is in the first position. Needle holder device 320 is then rotated 90° and inserted into a selected pair of needle holder device receiving cups 358. Alignment plate 315 is then advanced into the second position, thus capturing the needle holder device 320 into a selected parallel path.

After puncture device 325 is seated within a selected parallel path within guide tower 310 (e.g., within a selected pair of needle holder device receiving cups 358 and locked by alignment plate 315), guide tower 310 is slidingly advanced forward relative to guide platform 305 and the ultrasound probe to engage (e.g., puncture) the patient at a selected location. Guide tower 310 is further advanced until a tip of puncture device 325 reaches a desired depth within patient or until guide tower 310 abuts stabilization feature 335 at a front portion of guide platform 305.

Consistent with embodiments described herein, following patient puncture, alignment plate 315 may be returned to its first, non-locking position. Needle holder device 320 may then be pivoted about needle holder device receiving cups 358 or removed from needle holder device receiving cups 358 and moved to a new vertical position without requiring a second puncture.

Figure 5A:
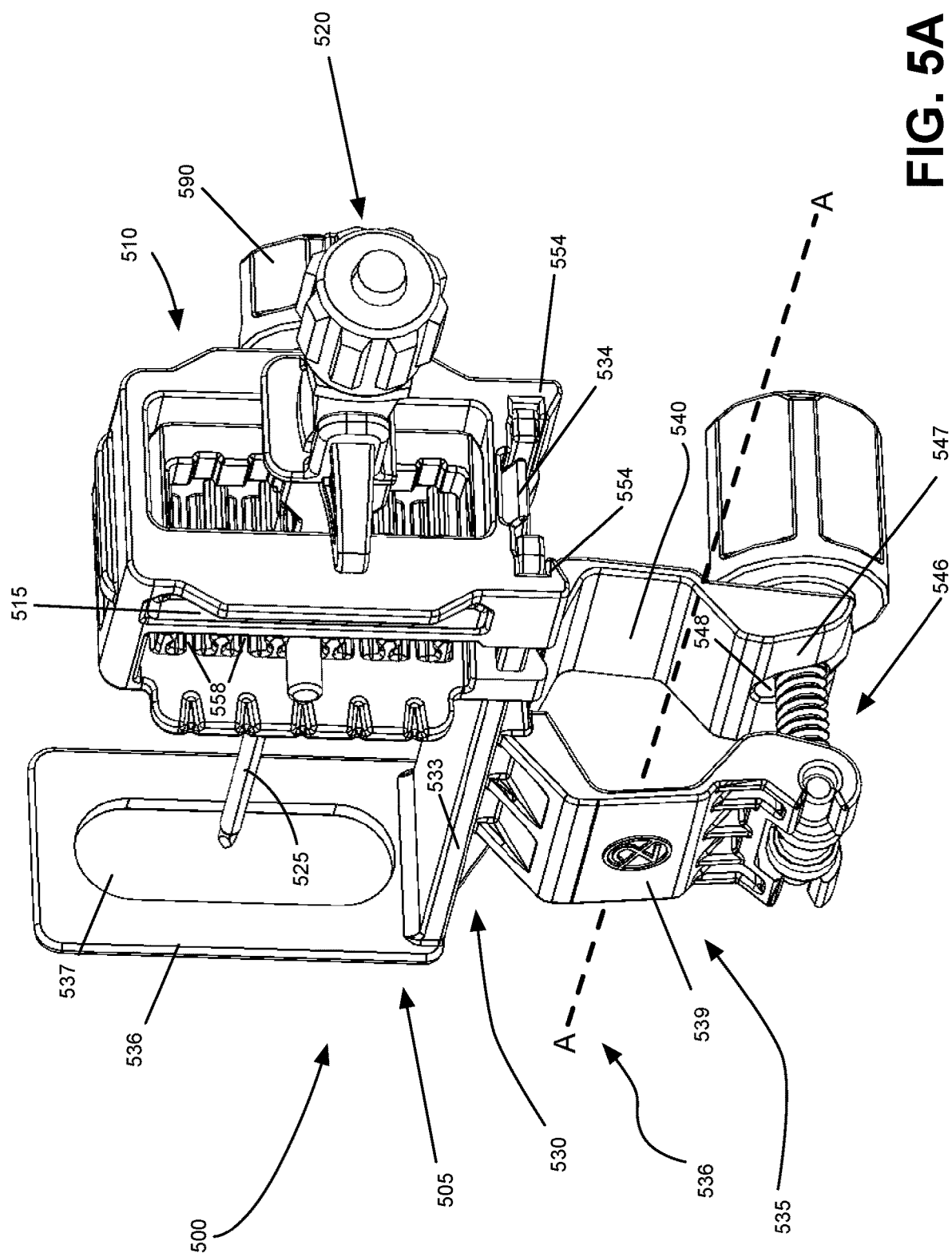
FIGS. 5A and 5B are isometric and exploded isometric views, respectively, illustrating another embodiment of a needle guidance device for use with an ultrasound probe, consistent with embodiments described herein.
Figure 5B:
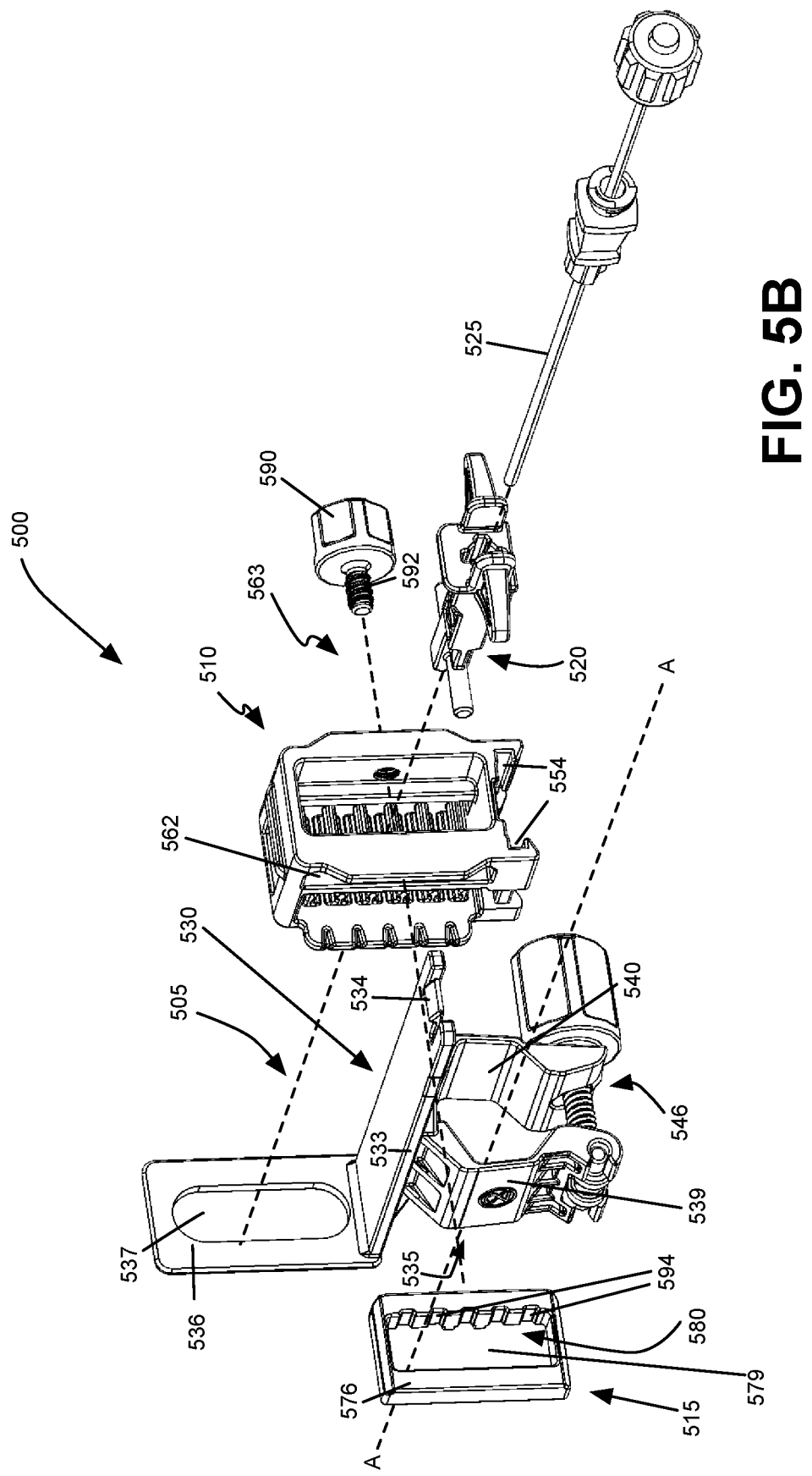

FIGS. 5A and 5B are isometric and exploded isometric views, respectively, illustrating another embodiment of a needle guidance device 500 for use with an ultrasound probe, consistent with embodiments described herein. As shown, needle guidance device 500 includes a guide platform 505, a guide tower 510, an alignment plate 515, and a needle holder device 520. Prior to use, guide platform 505 may be secured to an ultrasound probe (not shown) and guide tower 510 may be slidingly coupled to guide platform 505. Prior to administration, a needle or other type of puncture device 525, such as a trocar needle, may be coupled to a needle holder device 520, as described below. In some implementations, puncture device 525 may be formed together with needle holder device 520, as an integral unit, such that the puncture device 525 is not independently removable from needle holder device 520. The combined needle holder device 520 and puncture device 525 may be oriented within one of a plurality of path positions in guide tower 510. During use, guide tower 510 may be slidingly advanced forward relative to guide platform 505 and the ultrasound probe to engage the patient at a selected location. Upon completion of the procedure, the guide tower 510 may be retracted relative to guide platform 505 and the ultrasound probe to disengage puncture device 525 from the patient.

As shown in FIG. 5B, guide platform 505 includes a mount portion 530, a strap portion 535, and a securement portion 540. As described herein, mount portion 530 may include a longitudinally extruded configuration to support guide tower 510 in a longitudinally adjustable configuration. For example, as shown in FIG. 5B, lateral edges of mount portion 530 may form a pair of side rails 533. As described below, side rails 533 are configured for slidable receipt within corresponding side rails 554 or channels within in guide tower 510, as shown in FIG. 5A. To prevent guide tower 510 from moving too loosely relative to mount portion 530 during use, tolerances of respective side rails 533 may be such that a frictional relationship exists between mount portion 530 and guide tower 510 that resists undesirable movement. In some implementations, the relative dimension of mount portion 530 may be configured such that frictional resistance increases at a rearward end, to prevent inadvertent removal of guide tower 510 from mount portion 530. In other implementations, one or more stops, detents, or engagement portions may be provided on one or more of rails 533 and 554 to limit relative movement between guide tower 510 and guide platform 505. For example, as shown in FIGS. 5A-6B, a rearward end of mount portion 530 may include a resilient stop clip 534 the prevents removal of guide tower 510 from guide platform 505. When removal is necessary, clip 534 may be manually deflected downwardly, allowing guide tower 510 to be slidingly removed from guide platform 505.

As shown in FIGS. 5A and 5B, the forward end of mount portion 530 may include a stabilization feature 536 that projects perpendicularly upwardly from mount portion 530. In the illustrated embodiment, stabilization feature 536 includes a large central aperture or window 537 therein for allowing puncture device 525 to move freely therethrough. In other implementations, stabilization feature 536 may be provided on one lateral side of guide platform 505 relative to a puncture device path, such as stabilization feature 636 and aperture 637 shown in FIG. 6C. Although stabilization feature 636 shown in FIG. 6C includes a central aperture 637, in other implementations, no central aperture may be provided since puncture device 525 does not project through the stabilization feature, but rather passes to the side.

During use, a forward end of stabilization feature 536 is configured to engage a patient (e.g., a patient's perineum) to stabilize the relationship between needle guidance device 500 and the patient. In addition, a rearward end of stabilization feature 536 further provides a positive stop to longitudinal movement of guide tower 510 relative to guide platform 505. In some implementations, stabilization feature 536 may further include indexing indicia (e.g., numbers, markings, etc.) for allowing rapid confirmation of needle path at the point of penetration. In some implementations, such indexing indicia may be provided in a glow-in-the-dark printed format to facilitate visibility during use.

As shown in FIGS. 5A and 5B, strap portion 535 includes a pair of strap members 539 and 540, each of which are configured to at least generally correspond to a curved outer configuration of at least a portion of a transducer probe (not shown). In one implementation, strap members 539/540 are integrally formed with mount portion 530, as shown in FIGS. 5A-6B. In other implementations, lateral sides of mount portion 530 may include slots for receiving upper ends of strap members 539/540 to secure them to mount portion 530 in a pivotal manner.

Consistent with implementations described herein, a distance between strap portion 535 and a front end/stabilizing feature 536 of mount portion 530 is selected to optimize a working length of the ultrasound probe and needle guidance device 500. For example, in one implementation, a distance between a front end of strap portion 535 and a rear edge of stabilization feature 536 may range from about 0.5 to 1.0 inches and may preferably be a distance of 0.687 inches.

As shown, strap members 539/540 form a V platform capable of secure attachment to a variety of ultrasound probes having different diameters and configurations. Strap members 539/540 collectively terminate in securement portion 546. As shown in FIGS. 5A and 5B, in one implementation, securement portion 546 may include a collar portion 547 formed at the terminus of strap member 540 and a lock assembly 549 coupled to the terminus of strap member 539. Collar portion 547 may include an opening 548 adapted to receive a portion of lock assembly 549 during mounting of guide platform 505 onto the ultrasound probe, as described in additional detail below with respect to FIGS. 6A and 6B.

Figure 6B:
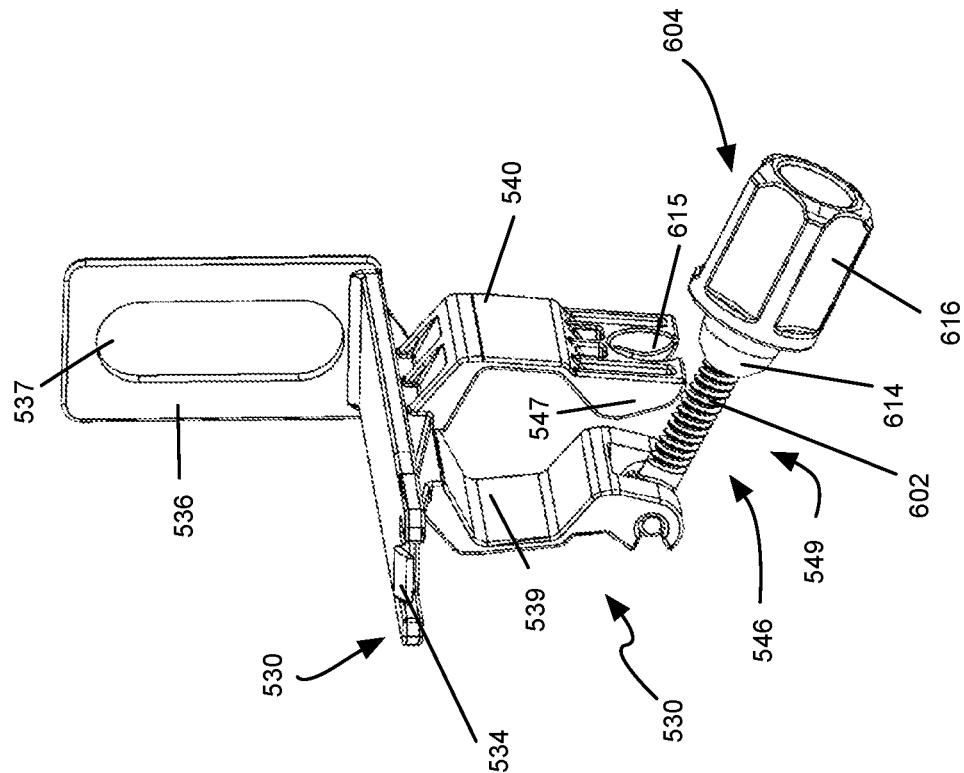
FIGS. 6A and 6B are isometric and reverse isometric views, respectively, of the guide platform of FIGS. 5A and 5B in an unlatched configuration.
Figure 6A:
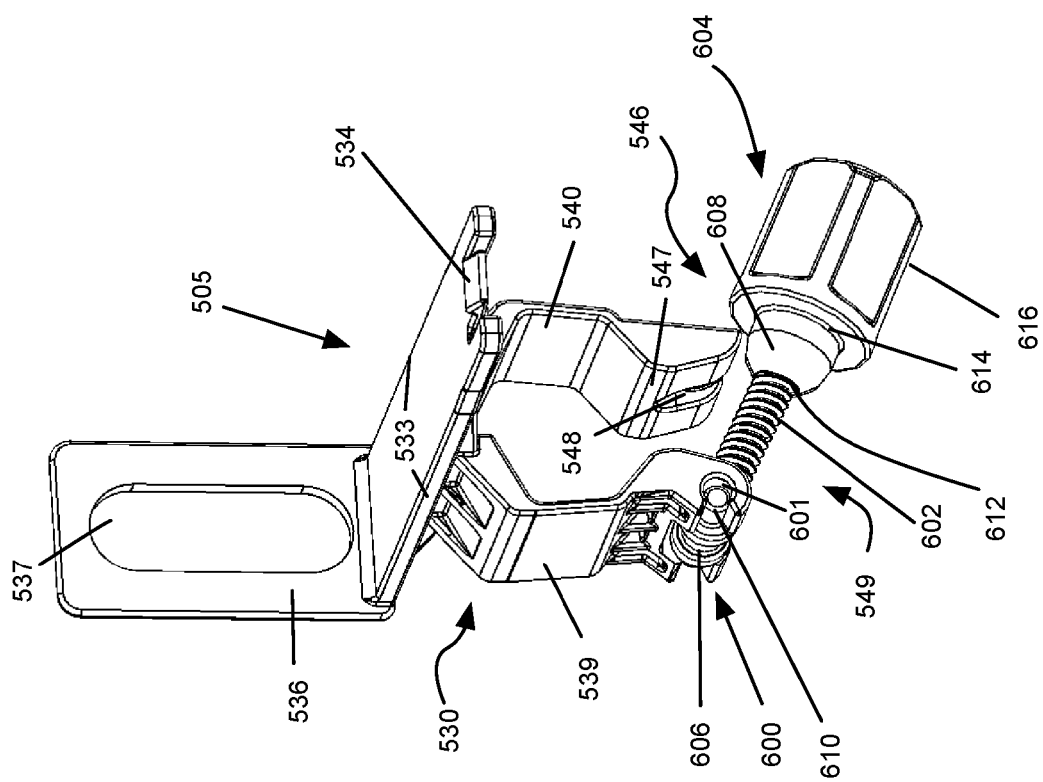
Figure 6C:
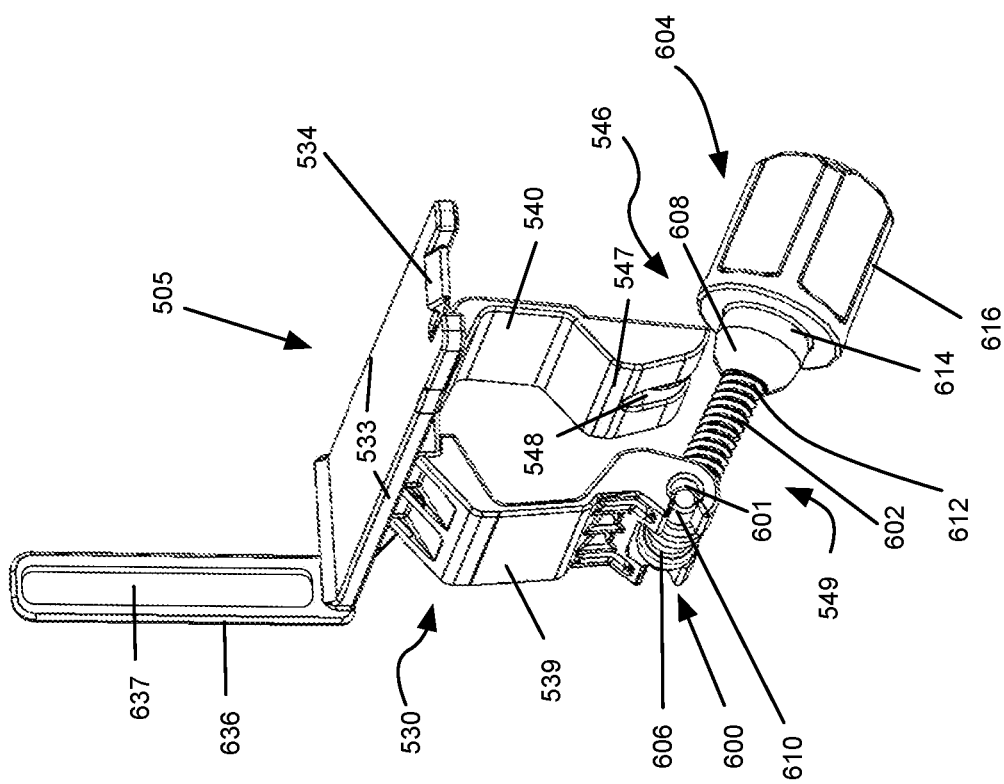
FIG. 6C is an isometric view of another embodiment of the guide platform of FIGS. 5A and 5B.

FIGS. 6A and 6B an isometric and reverse isometric views, respectively, of guide platform 505 in an unlatched configuration. As shown in FIGS. 5A, 5B, 6A, and 6B, lock assembly 549 includes a lock mounting portion 600, a threaded rod 602, and a thumb screw element 604. As shown in FIG. 6A, lock mounting portion 600 includes a portion of the terminus of strap member 539 that forms a receiving channel or opening for receiving a first end 606 of threaded rod 602 therein. In one implementation, lock mounting portion 600 includes a pair of opposing slotted apertures 601 for receiving corresponding portions of threaded rod 602, as described below.

As shown in FIG. 6A, threaded rod 602 includes a generally cylindrical threaded configuration having a first end 606 that engages with first strap member 539 and second end 608 that engages with second strap member 540. A pair of pivot elements 610 project outwardly from either side of first end 606 of threaded rod 602. Pivot elements 610 are configured to be received within apertures 601 in lock mounting portion 600 in first strap member 539.

As shown in FIG. 6B, thumb screw element 604 includes a threaded receiving aperture 612, a ball-type engagement interface 614, and a knob portion 616. Receiving channel 612 is configured to receive send end of 608 of threaded rod 602. Ball-type engagement interface 614 is configured to engage a semi-spherical engagement portion 615 in collar portion 547 in a ball-and-socket manner. Such a ball-and-socket type of clamping interface promotes a more uniform clamping force and feel across multiple clamp angles that need to be accommodated for clamping onto a range of probe shaft sizes and shapes.

To secure guide platform 505 to an ultrasound probe, threaded rod 602 is rotated about pivot elements 610 until second end 606 of threaded rod 602 enters opening 548 in collar portion 547. Knob portion 616 is then threadingly advanced on threaded rod 602, causing ball-type engagement interface 614 to engage semi-spherical engagement portion 615 in collar 547.

Consistent with implementations described herein, one or more of strap members 539/540 may be formed in a thickness sufficient to allow flexure. In some implementations, only one of strap members 539/540 is formed to enable flexure, with the other strap member 539/540 having a substantially rigid configuration.

Figure 7B:
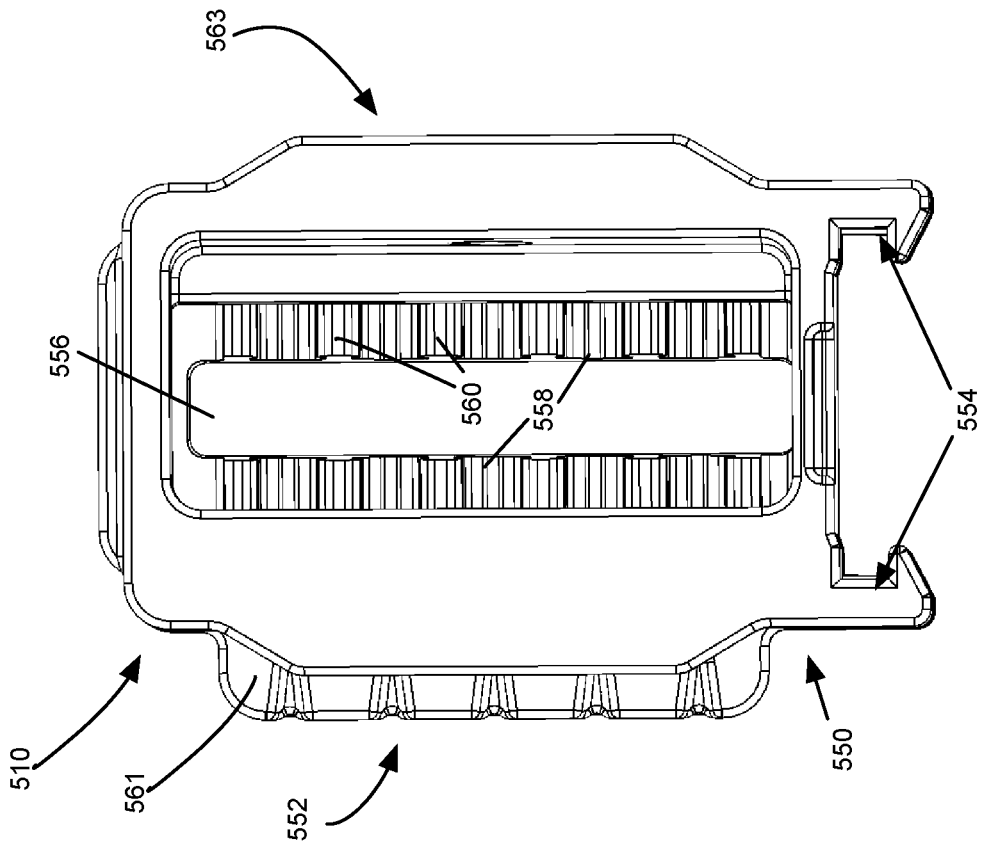
Figure 7A:
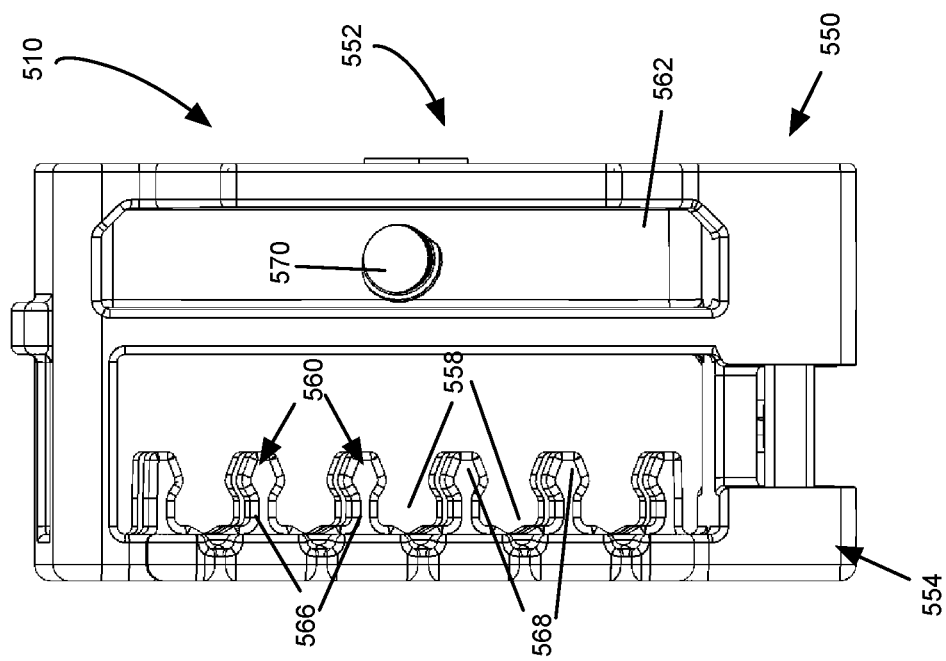

FIGS. 7A, 7B, and 7C are side plan, rear plan, and rear isometric views of guide tower 510 consistent with implementations described herein. As shown in FIGS. 5A, 5B, and 7A-7C, guide tower 510 includes a substantially frame-like configuration for providing a secure interface to guide platform 505 and a plurality of spaced (relative to a longitudinal orientation of the ultrasound probe, as depicted by line A-A in FIG. 5A) needle guide paths for engaging needle holder device 520, as described herein. In particular, guide tower 510 includes a platform interface portion 550 and a guide path portion 552 that projects upwardly from the platform interface portion 550. As briefly described above, a lower surface of platform interface portion 550 includes opposing side rails 554 that project downwardly therefrom and are configured to interface with side rails 533 in guide platform 505. In some implementations, side rails 554 have opposing c-shaped configurations that capture side rails 533 and prevent relative radial movement between guide platform 505 and guide tower 510 when side rails 533 in mount portion 530 are positioned within side rails 554 in guide tower 510, while allowing sliding longitudinal movement therebetween.

In one implementation consistent with embodiments described herein, guide path portion 552 projects upwardly substantially perpendicularly from platform interface portion 550. As shown in FIG. 7B guide path portion 552 includes a vertical guidance slot 556, a plurality of needle holder device receiving cups 558, a plurality of spring element portions 560, a guide tower engagement and indicia portion 561, an alignment plate receiving slot 562, and an alignment plate adjustment assembly 563.

Vertical guidance slot 556 is centrally aligned within guide tower 510 so as to be aligned with longitudinal ultrasound imaging crystals within a transducer to which the needle guide device 500 is affixed such that puncture device 525 designed to pass therethrough is consistently visualized in the imaging plane under typical imaging conditions. As shown in FIG. 9B, vertical guidance slot 556 extends substantially the entire height of guide tower 510 to allow an inserted puncture device to be freely moved between needle holder device receiving cup positions.

As shown in FIGS. 5B, 7B, and 7C, needle holder device receiving cups 558 comprise pairs of aligned recesses or openings in guide path portion 552 and positioned on opposite sides of vertical guidance slot 556. Consistent with implementations described herein, each needle holder device receiving cup 558 may comprises a generally arced or grooved opening configured to receive respective portions of needle holder device 520, as described below. Consistent with embodiments described herein, spring element portions 560 comprises pairs of resilient features positioned adjacent each needle holder receiving cup 558. As shown in FIG. 7C, spring element portions 560 project rearwardly and include a narrow deflecting portion 566 and a larger engagement end portion 568.

As described below, spring element portions 560 are configured to engage portions of needle holder device 520 so as to removably capture needle holder device in a selected pair of needle holder receiving cups 558. Each pair of needle holder device receiving cups 558/spring element portions 560 is vertically spaced relative to the adjacent pair of needle holder device receiving cups 558/spring element portions 560 to provide a plurality of attachment positions for needle holder device 520, as described in additional detail below. In the present embodiment, five pairs of needle holder device receiving cups 558 are provided, although other implementations may include fewer or additional needle holder device receiving cups 558 may be provided.

As shown in FIGS. 5B, 7B, and 7C, guide tower engagement and indicia portion 561 may include a portion of guide tower 510 that projects outwardly adjacent receiving cups 558/spring element portions 560. Guide tower engagement and indicia portion 561 may form an engagement surface for use in advancing or retracting guide tower 510 along guide platform 505. In addition, guide tower engagement and indicia portion 561 may include indicia and or markings indicative of a relative position of an inserted needle holder device 520.

As shown in FIG. 5B, alignment plate receiving slot 562 is formed on one side of guide tower 510 in a position rearward of needle holder device receiving cups 558. Alignment plate receiving slot 562 is sized to receive alignment plate 515 therein. Alignment plate adjustment assembly 563 is formed on an opposite side of guide tower 510 from alignment plate receiving slot 562 and includes a threaded aperture 570 and an adjustment knob 590. Threaded aperture 570 is laterally aligned with alignment plate receiving slot 562 and is configured to receive a threaded bolt 592 that projects from adjustment knob 590.

Upon receipt of a needle holder device 520 and corresponding puncture device 525 within a particular pair of needle holder device receiving cups 558/spring element portions 560, alignment plate 515 may be advanced within alignment plate receiving slot 562 by rotating adjustment knob 590 to positively support puncture device 525 at a selected location/orientation relative to ultrasound probe. Consistent with the embodiment of FIGS. 5A-7E, alignment plate 515 may positively retain puncture device 525 at any selected path.

FIGS. 7D and 7E are isometric and top plan views, respectively, of needle holder device 520 consistent with embodiments described herein. As shown in FIGS. 5A, 5B, 62D, and 7E, needle holder device 520 comprises an adapter for coupling to guide tower 510 and for receiving puncture device 525. In some implementations, needle holder device 520 may be configured to receive a puncture device therethrough. In one implementation, needle holder device 520 includes a body portion 700, engagement shoulders 702, alignment plate engagement portion 704, and needle receiving portion 706. As shown, body portion 700 includes a generally tubular element having a central aperture 708 therethrough. Body portion 700 is configured to receive puncture device 525 within central aperture 708. In some implementations, body portion 700 may include engagement elements 707 (e.g., tabs, ears, etc.) for facilitating insertion into and manipulation within guide tower 510.

A forward end of body portion 700 terminates in engagement shoulders 702 and a rearward end of body portion 700 terminates in needle receiving portion 706, which may be manipulated to effect proper placement of needle holder device 520 during use. For example, engagement elements 707 in body portion 700 may be used to insert and remove engagement shoulders 702 from needle holder device receiving cups 558, to rotate needle holder device 520 to allow removal from guide tower 510, to raise and lower needle holder device 520 between needle holder device receiving cups 558 and to affect manual angular deflection of needle holder device 520. In some implementations, needle receiving portion 706 may include one or more rotation-fixing elements, such as slots, keys, clips, threads, etc., for receiving a corresponding structure in puncture device 525 to prevent axial rotation and/or longitudinal movement of puncture device 525 relative to needle holder device 520.

Engagement shoulders 702 include a pair of substantially cylindrical elements that project perpendicularly outwardly from opposing sides of the forward end of body portion 700. As shown in FIG. 5A and described generally above, engagement shoulders 702 are configured to be received within a selected pair of needle holder device receiving cups 558 during use. The cylindrical configuration of engagement shoulders 702 allows for upward and downward rotation of needle holder device 520 within receiving cups 558 via body portion 700 if desired, and prior to advancement of alignment plate 515 within alignment plate receiving slot 562, which fixes the angular orientation of needle holder device 520. In some implementations, engagement shoulders 702 may include angle limiting portions 716 that project rearwardly from therefrom and are configured to engage portions of needle holder device receiving cups 558 to limit rotational movement of needle holder device 520 within needle holder device receiving cups 558.

As shown in FIGS. 5A and 7E, alignment plate engagement portion 704 is formed in body portion 700 and includes a generally rectangular configuration for engaging a portion of alignment plate at a particular path location. Alignment plate engagement portion 704 may further include a parallel path alignment feature 718 provided longitudinally on one side thereof, as shown in FIG. 7D. As described below, parallel path alignment feature 718 may positively engage one of a plurality of detents or notches 594 in alignment plate that correspond to needle holder device receiving cups 558/spring element portions 560, as described below.

As shown in FIG. 5B, alignment plate 515 includes a body portion 576, a free movement portion 579 and a needle holder device engagement portion 580. In general, alignment plate body portion 576 includes a substantially planar element sized for receipt within alignment plate receiving slot 562. Consistent with implementations described herein, free movement portion 579 includes an opening through alignment plate 515 that allows unfettered movement of needle holder device 520. Needle holder device engagement portion 580 includes an inside surface of free movement portion 579 configured to clampingly engage alignment plate engagement portion 704 of needle holder device 520. As described briefly above, needle holder device engagement portion 580 may include a plurality of notches or detents 594 that correspond with needle holder device receiving cups 558/spring element portions 560. Notches 594 are configured to engage path alignment feature 718 in alignment plate engagement portion 704 to maintain needle holder device in a selected parallel path orientation. In some implementations (not shown), alignment plate body portion 576 may include a tab or other engagement means that extends through alignment plate slot 562 for use in moving guide tower 510 longitudinally forward and rearward on guide platform 505.

When a user wishes to establish a parallel needle path, the user may rotate needle holder device 520 so as to align parallel path alignment feature 718 with a particular detent or notch 594 that corresponds to the desired parallel path. Upon tightening of knob 590, alignment plate 515 may be urged toward needle holder device 520, causing parallel path alignment feature 718 to seat within the particular detent or notch 594. Continued tightening of knob 592 effectively clamps needle holder device 520 at the desired position.

Conversely, when a user wishes to establish a non-parallel needle path, the user may rotate needle holder device 520 to a desired non-parallel orientation. In such an orientation, parallel path alignment feature 718 is not aligned with any of notches 594. Upon tightening of knob 590, alignment plate 515 may be urged toward needle holder device 520, causing needle holder device engagement portion 580 to clampingly engage path alignment feature 704/718. Continued tightening of knob 590 effectively clamps needle holder device 520 at the desired position.

Figure 8:
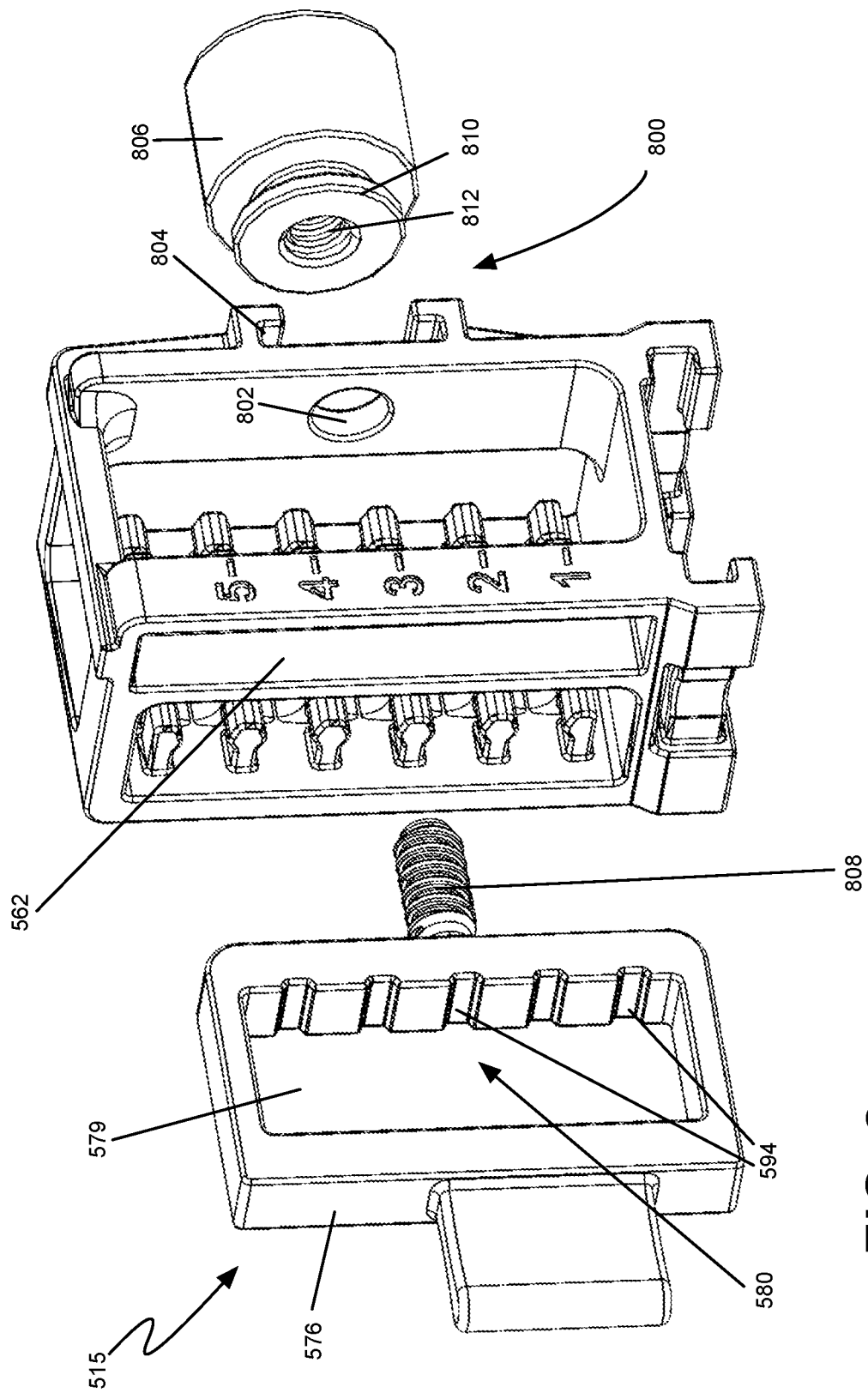
FIG. 8 is an isometric view of an alternative embodiment of a guide tower consistent with implementations described herein.

FIG. 8 is an isometric view of an alternative embodiment of guide tower 510 and alignment plate 515 consistent with implementations described herein. As shown in FIG. 8, guide tower 510, in contrast to the embodiment of FIGS. 5A-7E, includes alignment plate adjustment assembly 800 formed on an opposite side of guide tower 510 from alignment plate receiving slot 562. As shown, alignment plate adjustment assembly 800 includes an aperture 802, an adjustment knob retaining channel 804, and an adjustment knob 806. Aperture 802 is configured to receive a threaded bolt 808 that projects from alignment plate 515. In this implementation, adjustment knob 806 includes a flange portion 810 and a threaded aperture 812 for receiving threaded bolt 808. Flange portion 810 is received within adjustment knob retaining channel 804 to retain adjustment knob 806 at in a fixed lateral relationship with respect to guide tower 510 while simultaneously allowing adjustment knob 806 to rotate, which causes alignment plate 515 to move laterally within adjustment plate receiving slot 562.

Upon receipt of a needle holder device 520 and corresponding puncture device 525 within a particular pair of needle holder device receiving cups 558/spring element portions 560, alignment plate 515 may be advanced within alignment plate receiving slot 562 with adjustment knob 806 to positively support puncture device 525 at a selected location/orientation relative to an ultrasound probe. Consistent with the embodiment of FIGS. 5A-7E, alignment plate 515 may positively retain puncture device 525 at any selected path.

After puncture device 525 is seated within a selected parallel path within guide tower 510 (e.g., within a selected pair of needle holder device receiving cups 558 and locked by alignment plate 515), guide tower 510 is slidingly advanced forward relative to guide platform 505 and the ultrasound probe to engage (e.g., puncture) the patient at a selected location. Guide tower 510 is further advanced until a tip of puncture device 525 reaches a desired depth within patient or until guide tower 510 abuts stabilization feature 536 at a front portion of guide platform 305.

Consistent with embodiments described herein, following patient puncture, adjustment knob 590 may be rotated to return alignment plate 515 to its first, non-locking position. Needle holder device 520 may then be pivoted about needle holder device receiving cups 558 or removed from needle holder device receiving cups 558 and moved to a new vertical position without requiring a second puncture.

The foregoing description of exemplary implementations provides illustration and description but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A puncture device guide, comprising:
   a guide platform configured to releasably attach to an ultrasound probe;
   a guide tower slidingly coupled to the guide platform, wherein the guide tower is enabled to slide relative to the guide platform; and
   a needle holder device removably coupled to the guide tower,
   wherein the guide tower projects upwardly from the guide platform,
   wherein the guide tower includes a single vertical guidance slot and a plurality of vertical attachment positions at a plurality of spaced vertical locations within the vertical guidance slot, each vertical attachment position of the plurality of vertical attachment positions for engaging the needle holder device at a corresponding vertical position within the vertical guidance slot, wherein the needle holder device further comprises:

a body portion having a central aperture extending therethrough; and a pair of engagement shoulders extending outwardly from the body portion, wherein each vertical attachment position in the guide tower comprises a pair of arcuately shaped needle holder device receiving cups positioned on opposite sides of the vertical guidance slot to define a vertical distance from the ultrasound probe, and wherein an arcuate shape of each the pair of arcuately shaped needle holder device receiving cups is configured to pivotably receive a corresponding engagement shoulder of the pair of engagement shoulders in the needle holder device and the needle holder device is pivotably movable within the pair of needle holder device receiving cups between a plurality of path angles.

2. The puncture device guide of claim 1, wherein the guide platform comprises:

a mount portion for engaging the guide tower; and a strap portion coupled to the mount portion, wherein the strap portion permits releasable attachment to the ultrasound probe.

3. The puncture device guide of claim 2, wherein the mount portion comprises at least one side rail for slidingly engaging a corresponding at least one side rail on the guide tower.

4. The puncture device guide of claim 2, wherein a lower surface of the mount portion is configured to engage the ultrasound probe, and wherein the lower surface of the mount portion comprises a longitudinal channel for receiving an accessory device therethrough.

5. The puncture device guide of claim 2, wherein an upper surface of the mount portion comprises a stabilization element configured to engage at least one of a patient or the guide tower.

6. The puncture device guide of claim 5, wherein at least one of the stabilization element or the guide tower includes indexing indicia thereon.

7. The puncture device guide of claim 2, wherein an upper surface of the mount portion comprises a stop element for preventing relative movement between the guide tower and the guide platform.

8. The puncture device guide of claim 2, wherein an upper surface of the mount portion comprises a plurality of fixation elements projecting upwardly therefrom, wherein each fixation element of the plurality of fixation elements is configured to engage a spring clip element in a lower surface of the guide tower at a plurality of respective positions relative to the mount portion, to facilitate releasable securement of the guide tower relative to the guide platform as the guide tower is advanced through each respective position of the plurality of respective positions.

9. The puncture device guide of claim 2, wherein the strap portion further comprises:

a first lateral portion projecting from a first side of mount portion and a second lateral portion projecting from a second side of the mount portion, wherein the first lateral portion includes a collar portion having an opening therein, wherein the second lateral portion includes a threaded portion; and a clamping nut threadingly coupled to the threaded portion, wherein, during assembly, the opening in the collar portion receives the threaded portion and the clamping nut is advanced on the threaded portion to engage the collar portion.

10. The puncture device guide of claim 1, wherein the needle holder device comprises a funnel portion to facilitate entry of a puncture device into the central aperture.

11. The puncture device guide of claim 1, wherein each of the pair of arcuately shaped needle holder device receiving cups includes an angle restraining portion and wherein at least one of the pair of engagement shoulders in the needle holder device comprises an angle limiting portion configured to engage an angle restraining portion to limit pivoting rotation of the needle holder device relative to the arcuately shaped needle holder device receiving cups.

12. The puncture device guide of claim 1, further comprising:

a pair of spring element portions positioned adjacent the pair of arcuately shaped needle holder device receiving cups, wherein the pair of spring element portions include resilient elements configured to removably capture the needle holder device within the adjacent pair of arcuately shaped needle holder device receiving cups.

13. The puncture device guide of claim 1, further comprising:

an alignment plate, wherein the guide tower comprises an alignment plate receiving slot extending transversely therethrough, wherein the alignment plate comprises a body portion and a plurality of path retaining elements, a first path retaining element of the plurality of path retaining elements corresponding to the pair of arcuately shaped needle holder device receiving cups, wherein inserting the alignment plate into the alignment plate receiving slot causes the first path retaining element to align with the pair of arcuately shaped needle holder device attachment cups to define a corresponding path through the vertical guidance slot.

14. The puncture device guide of claim 13, wherein the first path retaining element comprises a path retaining channel formed within the body portion of the alignment plate, wherein the path retaining channel aligns with the pair of arcuately shaped needle holder device attachment cups.

15. The puncture device guide of claim 1, further comprising:

an alignment plate comprising a body portion, a free movement portion, and a plurality of path retaining elements projecting into the free movement portion, a first path retaining element of the plurality of path retaining elements corresponding to the pair of arcuately shaped needle holder device receiving cups, wherein the guide tower comprises an alignment plate receiving slot extending transversely therethrough; and an alignment plate adjustment knob, wherein rotation of the alignment plate adjustment knob causes the alignment plate to engage the body portion of the needler holder device, to retain the needle holder device at a selected position.

16. The puncture device guide of claim 15, wherein the body portion of the needle holder device further comprises a parallel path alignment feature, and wherein the first path retaining element is configured to selectively engage the parallel path alignment feature to retain the needle holder device in a parallel path orientation.

17. The puncture device guide of claim 15, wherein the guide tower comprises a threaded aperture aligned with the alignment plate receiving slot for receiving a threaded bolt therein, wherein the threaded bolt projects from the adjustment knob and engages the alignment plate to urge the first path retaining element in the alignment plate into engagement with the needle holder device at a desired path orientation.

18. The puncture guide device of claim 15, wherein the guide tower comprises an aperture aligned with the alignment plate receiving slot for receiving a threaded bolt therein, wherein the threaded bolt projects from the alignment plate and threadingly engages a threaded aperture in the adjustment knob to urge the first path retaining element in the alignment plate into engagement with the needle holder device at a desired path orientation.

19. A puncture device guide, comprising:

a guide platform having a surface and configured to releasably attach to an ultrasound probe;

a guide tower extending from the surface of the guide platform, the guide tower configured to slide along at least a portion of a length of the surface between a first position and a second position, the guide tower comprising: a single vertical guidance slot; and a plurality of pairs of aligned needle holder device receiving cups spaced at a plurality of vertical locations on the guide tower, each pair of aligned needle holder device receiving cups of the plurality of pairs of aligned needle holder device receiving cups comprising a first needle holder device receiving cup positioned on a first lateral side of the vertical guidance slot and a second needle holder device receiving cup positioned on a second lateral side of the vertical guidance slot opposite the first lateral side; and a needle holder device removably coupled to the guide tower, the needle holder device comprising a body portion and a pair of engagement shoulders extending outwardly from the body portion, wherein each pair of aligned needle holder device receiving cups is configured to receive the pair of engagement shoulders to retain the needle holder device within the vertical guidance slot at a corresponding vertical location of the plurality of vertical locations such that the needle holder device is pivotably movable at the corresponding vertical location between a first path angle with respect to the ultrasound probe and a second path angle with respect to the ultrasound probe different than the first path angle;

wherein the needle holder device receiving cups are arcuately shaped.

* * * * *